US012653855B2

(12) United States Patent
Backes

(10) Patent No.: US 12,653,855 B2
(45) Date of Patent: *Jun. 16, 2026

(54) OPTIMIZING VOLATILE ENTOURAGES IN DRY FLOWERING PLANT MIXTURES

(71) Applicant: Perfect Herbal Blends, Inc., Fallbrook, CA (US)

(72) Inventor: Michael Dane Backes, Fallbrook, CA (US)

(73) Assignee: Perfect Herbal Blends, Inc., Fallbrook, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 18/320,001

(22) Filed: May 18, 2023

(65) Prior Publication Data

US 2023/0285485 A1 Sep. 14, 2023

Related U.S. Application Data

(63) Continuation-in-part of application No. 17/560,057, filed on Dec. 22, 2021, now Pat. No. 11,654,170, which is a continuation of application No. 17/012,526, filed on Sep. 4, 2020, now Pat. No. 11,253,564.

(60) Provisional application No. 62/992,154, filed on Mar. 20, 2020, provisional application No. 62/896,775, filed on Sep. 6, 2019.

(51) Int. Cl.
| | |
|---|---|
| *A61K 36/185* | (2006.01) |
| *A24D 1/18* | (2006.01) |
| *A61K 31/01* | (2006.01) |
| *A61K 31/015* | (2006.01) |
| *A61K 31/045* | (2006.01) |
| *A61K 31/336* | (2006.01) |
| *A61K 31/352* | (2006.01) |

(52) U.S. Cl.
CPC ............ *A61K 36/3482* (2024.05); *A24D 1/18* (2013.01); *A61K 31/01* (2013.01); *A61K 31/015* (2013.01); *A61K 31/045* (2013.01); *A61K 31/336* (2013.01); *A61K 31/352* (2013.01); *A61K 36/185* (2013.01); *A61K 36/3486* (2024.05); *A61K 2236/15* (2013.01); *A61K 2236/17* (2013.01); *A61K 2236/35* (2013.01)

(58) Field of Classification Search
CPC ............... A61K 36/185; A61K 31/352; A61K 2236/15; A61K 2236/17
See application file for complete search history.

(56) References Cited

U.S. PATENT DOCUMENTS

| | | | |
|---|---|---|---|
| 7,363,929 B2 | 4/2008 | Fagg et al. | |
| 9,095,554 B2 | 8/2015 | Lewis et al. | |
| 9,370,164 B2 | 6/2016 | Lewis et al. | |
| 9,642,317 B2 | 5/2017 | Lewis et al. | |
| 9,649,349 B1 | 5/2017 | Tucker et al. | |
| 9,730,911 B2 | 8/2017 | Verzura et al. | |
| 9,919,241 B1 | 3/2018 | Auerbach et al. | |
| 10,092,852 B2 | 10/2018 | Tucker | |
| 10,238,706 B1 | 3/2019 | Nahtigal | |
| 10,315,129 B1 | 6/2019 | Auerbach et al. | |
| 10,323,014 B2 | 6/2019 | Robertson et al. | |
| 2006/0090769 A1 | 5/2006 | Woodson et al. | |
| 2010/0116281 A1 | 5/2010 | Marshall et al. | |
| 2016/0106705 A1 | 4/2016 | Verzura et al. | |
| 2016/0366926 A1 | 12/2016 | Uren | |
| 2017/0008870 A1 | 1/2017 | Dibble et al. | |
| 2017/0266245 A1 | 9/2017 | Scialdone | |
| 2017/0273349 A1 | 9/2017 | Moore | |
| 2017/0333503 A1 | 11/2017 | Ayres | |
| 2017/0360861 A1 | 12/2017 | Humphreys et al. | |
| 2017/0367408 A1 | 12/2017 | Pang et al. | |
| 2018/0143212 A1 | 5/2018 | Giese et al. | |
| 2018/0169035 A1 | 6/2018 | Eyal | |
| 2018/0280459 A1 | 10/2018 | Eyal | |
| 2018/0284145 A1 | 10/2018 | Giese et al. | |
| 2018/0289062 A1 | 10/2018 | Lopez | |
| 2018/0296616 A1 | 10/2018 | Rivas | |
| 2018/0296617 A1 | 10/2018 | Rivas | |
| 2018/0343901 A1 | 12/2018 | Leo et al. | |
| 2018/0344785 A1 | 12/2018 | Robertson | |
| 2018/0369191 A1 | 12/2018 | Muscarella et al. | |
| 2019/0022158 A1 | 1/2019 | Greenbaum et al. | |
| 2019/0105859 A1 | 4/2019 | Dunn | |
| 2019/0192422 A1 | 6/2019 | Shibaz et al. | |

FOREIGN PATENT DOCUMENTS

| | | |
|---|---|---|
| WO | WO 2014/159688 A1 | 10/2014 |
| WO | WO 2017/193072 A1 | 11/2017 |
| WO | WO 2018/112479 A1 | 6/2018 |
| WO | WO 2018/195562 A1 | 10/2018 |
| WO | WO 2018/226899 A1 | 12/2018 |

(Continued)

OTHER PUBLICATIONS

Wianowska et al., "Transformations of Tetrahydrocannabionl, Tetrahydrocannabinolic Acid and Cannabinol during Their Extraction from *Cannabis sativa* L.", Journal of Analytical Chemistry, 2015, vol. 70, No. 8, pp. 920-925.

McPartland et al., "A Classification of endangered high-THC cannabis (*Cannabis sativa* subsp. indica) domesticates and their wild relatives", PhytoKeys,144: 81-112, Apr. 3, 2020.

McPartland et al., Supplementary materials to "A Classification of endangered high-THC cannabis (*Cannabis sativa* subsp. indica) domesticates and their wild relatives", PhytoKeys,144: 81-112, Apr. 3, 2020.

Bottger, Angelika et al., "Lessons on Caffeine, Cannabis & Co, Plant-derived Drugs and their Interaction with Human Receptor," Learning Materials in Biosciences, Springer, 2018.

(Continued)

*Primary Examiner* — Sahar Javanmard

(74) *Attorney, Agent, or Firm* — Gerald T. Gray; Leydig, Voit & Mayer, LTD

(57) ABSTRACT

Novel fragrant and flavorful *Cannabis* plant products with defined chemistry customized to provide a desired, consistent and stable Entourage of Interest (EOI) and processes for making and using the same are provided.

25 Claims, No Drawings

(56)             References Cited

FOREIGN PATENT DOCUMENTS

| WO | WO 2019/034936 A2 | 2/2019 |
| WO | WO 2019/113574 A1 | 6/2019 |
| WO | WO 2019/130201 A1 | 7/2019 |
| WO | WO 2019/133952 A2 | 7/2019 |

OTHER PUBLICATIONS

Marina Santiago, et al., "Absence of Entourage: Terpenoids Commonly Found in Cannabis sativa Do Not Modulate the Functional Activity of D9-THC at Human CB1 and CB2 Receptors." Cannabis and Cannabinoid Research. vol. 4, No. 3, 165-176, 2019.

Morgan, Celia J. A. et al., "Individual and combined effects of acute delta-9-tetrahydrocannabinol and cannabidiol on psychotomimetic symptoms and memory function," Translational Psychiatry 8:181, 2018.

Wise, Kimber et al., "Inhalation Absorption Prediction (IAP) Model for Predicting Medicinal Cannabis Phytochemical Pharmacokinetics", Pharmacogn. Commn. 2019; 9(3): 85-90, Jun. 2019.

Cunningham, Christopher W., "Plant-Based Modulators of Endocannabinoid Signaling", J. Nat. Prod., 82, 3, 636-646, 2019.

McPartland, John M. et al., "Care and Feeding of the Endocannabinoid System: A Systematic Review of Potential Clinical Interventions that Upregulate the Endocannabinoid System" PLoS One. 9(3):e89566, pub. Mar. 12, 2014.

Mudge EM, et al."The Terroir of Cannabis: Terpene Metabolomics as a Tool to Understand Cannabis sativa Selections", Planta Med. 85(9-10):781-796, Apr. 30, 2019.

Chandra, S, et al. "Cannabis sativa L.—Botany and Biotechnology," Springer International Publishing AG, 2017.

Small, E., "Cannabis A Complete Guide," Agriculture and Agri-Food Ottawa, Ontario, Canada, CRC Press Taylor & Francis Group, pub. Oct. 14, 2016.

Russo, E. (2019) "The Case for the Entourage Effect and Conventional Breeding of Clinical Cannabis: No Strain," No Gain, Front Plant Sci. Jan 9;9:1969, 2019.

Labate, Beatriz Caiuby, et al. Eds., "Plant Medicines, Healing and Psychedelic Science Cultural Perspective," Springer International Publishing AG, 2018.

Hillig et al., "A Chemotaxonomic Analysis of Cannabinoid Variation in Cannabis (Cannabaceae)" American Journal of Botany 91(6): 966-975, 2004.

de Meijer et al., "The inheritance of chemical phenotype in Cannabis sativa L" Genetics Society of America, 163(1):335-46, 2003.

de Meijer et al., "The inheritance of chemical phenotype in Cannabis sativa L. (II): Cannabigerol predominant plants" Euphytica, 145:189-198, 2005.

Mandolino et al.,"Potential of marker-assisted selection in hemp genetic improvement" Euphytica 140, pp. 107-120, Jan. 2004.

Staginnus, C. et al., "A PCR marker linked to a THCA synthase polymorphism is a reliable tool to discriminate potentially THC-rich plants of Cannabis sativa " J Forensic Sci. 59(4): 919-26, 2014.

de Meijer et al., "The inheritance of chemical phenotype in Cannabis sativa L. (Iv): cannabinoid- free plants" Euphytica, 168: 95-112, pub. Jan. 31, 2009.

de Meijer et al., "The inheritance of chemical phenotype in Cannabis sativa L. (V): regulation of the propyl-/pentyl cannabinoid ratio, completion of a genetic model," Euphytica, 210. 291-307, May 7, 2016.

Lewis, M. et al., "Pharmacological Foundations of Cannabis Chemovars," Planta Medica 84(4) 225-233, published Nov. 21, 2017.

Fischedick, Justin T., (2017) "Identification of Terpenoid Chemotypes Among High O-trans-D9—Tetrahydrocannabinol-Producing Cannabis sativa L. Cultivars" Cannabis and Cannabinoid Research 2.1: 34-47, 2017.

https://www.alchimiaweb.com/blogen/make-ice-water-hash/, Alchimiaweb S.L. Grow Shop, Girona, Spain, Alchimiaweb S.L. • CIF: B-17664368, 2001-2021.

https://www.alchimiaweb.com/blogen/make-thca-crystals-solventless-sauce/, Alchimiaweb S.L. Grow Shop, Girona, Spain, Alchimiaweb S.L. • CIF: B-17664368,2001-2021.

Stith, S. et al.,The Association between Cannabis Product Characteristics and Symptom Relief Sci Rep (2019) 9:2712, published Feb. 25, 2019.

Nuutinen T. "Medicinal properties of terpenes found in Cannabis sativa and Humulus lupulus" Eur J Med Chem. 157:198-228, Jul. 31, 2018.

Pertwee, Roger, "Handbook of Cannabis," Oxford University Press, Oxford, United Kingdom, 2014.

Russo et al., "Cannabis Pharmacology: The Usual Suspects and a Few Promising Leads," Adv Pharmacol. 2017:80:67-134, Jun. 5, 2017.

International Search Report for International application PCT/US2020/049508, dated Mar. 24, 2021 from the International Searching Authority.

Written Opinion for International application PCT/US2020/049508, dated Mar. 24, 2021 from the International Searching Authority.

U.S. Appl. No. 17/560,057, filed Dec. 22, 2021.

U.S. Appl. No. 17/012,526, filed Sep. 4, 2020.

Backes, "Cannabis Pharmacy: The Practical Guide to Medical Marijuana," Black Dog & Leventhal Publishers, Sep. 2014, revised Dec. 2017.

1

OPTIMIZING VOLATILE ENTOURAGES IN DRY FLOWERING PLANT MIXTURES

CROSS-REFERENCE TO RELATED APPLICATIONS

This application is a continuation-in-part of U.S. application Ser. No. 17/560,057, filed Dec. 22, 2021, which is a continuation of U.S. application Ser. No. 17/012,526, filed Sep. 4, 2020, which claims the benefit of U.S. Provisional Application No. 62/896,775, filed Sep. 6, 2019, and U.S. Provisional Application No. 62/992,154, filed Mar. 20, 2020, and, all of which are incorporated herein by reference in their entirety.

FIELD

The disclosure relates to novel plant products customized to provide a desired, consistent and stable Entourage of Interest (EOI) and processes for making the same.

BACKGROUND

There is a strong consumer demand for *Cannabis*-based plant products and an increasing appreciation for the diverse spectrum of compounds in *Cannabis* and other oil-producing plants together with their biological (physiological) and psychological effects. Attention is increasingly focused on the many compounds in the plant, how they may influence one another and the potential for beneficial effects when combinations of compounds are consumed (the "entourage effect"). This observation only scratches the surface of possible synergies available by way of combination of the wide scope of compounds found in *Cannabis* and other oil-producing plants.

Previous and current efforts known and popular in the art of *Cannabis* product development have focused on generation of genetic crosses of cultivars with attractive chemotypes, and/or addition of extracts or chemical additives to plant material to make up for compounds lost in processing.

Progress on breeding and genetics as a way to produce plant material that meets the needs of consumers has been slow. Until recently, informal breeding has been the norm where the main selection criteria for desirable cultivars has been morphology, aroma, and THC potency. In general, plant breeders have not considered the importance of good analytics tied to time-of-harvest and documented growing conditions, such as light, climate, nutrients, soil and the like. In addition, challenges have arisen with the stabilization of crosses with attractive chemotypes, viral, fungal and pest infestations, and the limited parental gene pool available for crosses. Mudge et al., Planta Medica 2019; 85(09/10): 781-796, present extensive data on analysis of low abundance terpenes associated with cannabinoid potency and suggest that informal breeding and selection has impacted phytochemical diversity in *Cannabis.*

As is typical of high value crops such as wine and hops, the aroma (fragrance) and the flavor of *Cannabis* is tied to volatile constituents referred to herein as "fragrant and flavorful compounds". In *Cannabis*, one type of fragrant and flavorful compound, the terpenes which includes monoterpenes, diterpenes, sesquiterpenes, terpenoids, and terpene alcohols, are mostly found in glandular trichomes collocated with cannabinoids, and maintenance of these valuable terpenes in processing fresh plant material has been challenging.

There remains a need for *Cannabis* and other oil-producing plant products that maximize pharmacology, flavor and fragrance in an Entourage of Interest (EOI), where the EOI can be customized to match the desire of medical and recreational *Cannabis* consumers, and the EOI is provided on a consistent and stable basis. The current disclosure addresses this need.

BRIEF SUMMARY

The present disclosure provides fragrant and flavorful *Cannabis* plant products with a formulation having defined chemistry. The products and processes detailed herein rely on an Entourage of Interest (EOI) extract from one or more marijuana or hemp plant types comprising one or more lipids and one or more fragrant and flavorful compounds. The EOI extract may be mixed with dried and chopped plant material from one or more *Cannabis* plant types wherein one or more fragrant and flavorful compounds, (terpenes (monoterpenes, diterpenes, sesquiterpenes, terpenoids, and terpene alcohols), esters, ethers, thiols, and aldehydes, are stably maintained in the *Cannabis* plant product when the plant product is stored at room temperature for 30 days or longer.

According to some embodiments, the EOI extract comprises one or more lipids, and one or more components of the plant-associated chemical and biological ecology, wherein one or more components of the plant-associated chemical and biological ecology are stably maintained in the *Cannabis* plant product when the plant product is stored at room temperature for 30 days or longer.

According to some embodiments, the EOI extract includes THCa, and the EOI extract is treated to reduce the amount of THCa resulting in a THCa-reduced EOI extract.

According to some embodiments, the EOI extract, the dried and chopped plant material substrate or the *Cannabis* plant product is supplemented with THCa or THC, which may be crystalline THCa and/or a cannabinoid isolate or distillate.

According to some embodiments, the total cannabinoid content in the *Cannabis* plant product is from about 0.1% to 45% cannabinoids, the total monoterpene content in the *Cannabis* plant product is from 1% to 10%, and the total sesquiterpene content in the *Cannabis* plant product is less than 2%.

According to some embodiments, the terpenes in the *Cannabis* plant product include one or more of β-caryophyllene, β-myrcene, limonene, linalool, α-humulene, β-pinene, α-pinene, α-bisabolol, α-terpinene, β-ocimene, camphene, caryophyllene oxide, cis-nerolidol, γ-3-carene, eucalyptol, γ-terpinene, geraniol, ocimene, (−)-guaiol, (−)-isopulegol, p-cymene, terpinolene, trans-nerolidol, gerol, geranyl acetate, α-terpineol, α-phellanderene, sabinene, thymol, cedrene, cedrol, fenchol, valencene, α-thujene, and cymene.

According to some embodiments, the formulation having defined chemistry is a formulation that targets dopamine receptors, a formulation that targets mu-opioid receptors, a formulation that targets 5-HT2A receptors, or a formulation that targets or encourages the formation of CB1/5-HT2A dimers.

According to some embodiments, the formulation having defined chemistry facilitates dimer formation between pairs of receptors including, dopamine receptors, CB1 receptors, serotonin receptors, adenosine receptors, opioid receptors, GABA receptors, glutamate receptors, and ion channels receptors.

According to some embodiments, the fragrant and flavorful *Cannabis* plant product further comprises from about 0.2 to 4.0% micro pulverized *Cannabis* leaf, a sealer coating comprising a plant cellulose compound, and the dried and chopped plant material may include one or more of hops, basil, mimosa, passion flower, corn silk, rose petals, lotus leaf, licorice root, jasmine, ginseng, red clover flowers, bergamot, lemon, lime, sweet orange, tangerine, mandarin, cinnamon bark, citronella, lemongrass, petitgrain, palmarosa, patchouli leaves, geranium, lavender, rosemary, spike lavender, ginger, vetiver, jasmine, neroli (orange blossom), and ylang-ylang.

According to some embodiments, the fragrant and flavorful EOI extract having defined chemistry, may be shipped in compliance with local, state, federal and international regulations.

DETAILED DESCRIPTION

Introduction

Disclosed herein are processes for supplementing a selected EOI at amounts found in a living plant and stabilizing the selected EOI in *Cannabis* plant products comprising dried *Cannabis* plant material and *Cannabis* extracts, plant products made using such processes, and plant products containing a selected EOI. The EOI is the desired and recoverable portion of all plant compounds that impact one or more of physiological effect, pleasure effect, psychological effect, and fragrance and flavor effect. The EOI comprises one or more terpenes, terpenoids, terpene alcohols, esters, ethers, thiols and aldehydes (fragrant and flavorful compounds), lipids, cannabinoids, and may also include compounds that are part of the plant-associated chemical and biological ecology.

Current practices for preparing dried *Cannabis* plant material often rely on harvesting, transporting, granulating, milling, grinding or chopping, and storage under conditions where all or part of its original EOI is lost. In addition, current *Cannabis* plant products such as pre-rolls are made in a manner that results of loss of the fragrant and favorable compounds that are important to the EOI.

The disclosure provides a *Cannabis* plant product with an introduced EOI which has the unexpected property of an EOI that is customized, produced consistently and with greater stability. The EOI or a fraction of the EOI may equal or exceed the EOI or fraction of the EOI found in the living plant.

Definitions

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited.

In the methods or processes described herein, the steps can often be carried out in any order without departing from the principles of the disclosure, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a step" includes single or plural steps and is considered equivalent to the phrase "comprising at least one step."

The term "or" refers to a single element of stated alternative elements or a combination of two or more elements, unless the context clearly indicates otherwise. As used herein, "comprises" means "includes". Thus, "comprising terpenes", means "including terpenes", without excluding additional elements. All references, including journal articles, patents, and patent publications cited herein are incorporated by reference in their entirety as if each individual journal article, patent, or patent publication, was specifically and individually indicated to be incorporated by reference in its entirety for all purposes.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

The term "accession" is used herein with reference to a group of related plant material from a single species which is collected at one time from a specific location.

The term "cannabinoids" is used herein with reference to one or more of THCa, THCVa, Δ9-THC, Δ8-THC, THCV, CBDa, CBD, CBDVa, CBDV, CBN, CBGVa, CBGa, CBGV, CBG, CBCVa, CBCV, CBCa, and CBC.

The term "*Cannabis* plant types" is used herein with reference to *Cannabis* plant types that are not a hybrid of at least two of *Cannabis sativa, Cannabis indica*, and *Cannabis ruderalis*. The term *Cannabis* plant types may be used with reference to marijuana, hemp or both.

The term "*Cannabis* plant product" may be used herein with reference to compositions that comprise dried and chopped plant material and an EOI extract, or compositions that comprise an EOI extract alone.

The term "chemotype" is used herein with reference to a type of plant expressing a distinctive group of chemical compounds.

The term "cold infused flower" is used is used herein with reference to plant flower material that has been chilled or frozen at the time of harvest, stored under cold conditions or frozen resulting in a product comprising a specific EOI.

The term "cultivar" is used is used herein with reference to a group of plants that exhibit common and distinguishable characteristics and that have been selected by breeding (also referred to as crossing).

The term "cultivated plant type" is used herein with reference to a plant of a particular cultivar or having a particular chemotype.

The term "entourage effect" as used herein means the combinatory biological (physiological) and psychological effect of consumption of phytochemicals found in oil-producing plants such as *Cannabis*.

The term "Entourage of Interest" or "EOI" as used herein means the desired and recoverable portion of all plant compounds that impact the physiological, psychological, or drug effect, hedonic effect, and/or fragrance and flavor effect. EOI compounds such as lipids may contribute to preservation and/or stabilization of the fragrant and flavorful compounds in a *Cannabis* plant product such that formulations having defined chemistry may be produced on a consistent basis.

The term "EOI metric" or "EOI level" is used herein with reference to the amount of selected plant compounds analyzed and quantified as an approximation of the total EOI.

The term "expelling" is used herein with reference to a mechanical, chemical-free process used to remove the oil from plant material. For example, expeller pressing may be used to squeeze the oil from a plant source under mechanical pressure in a temperature-controlled setting.

The term "formulation having defined chemistry" is used herein with respect to the specific combination of chemical components in a fragrant and favorable *Cannabis* plant product that result in the EOI. Formulations having defined chemistry result in consistent *Cannabis* plant products.

The term "fragrant and flavorful compounds", as used herein means terpenes (monoterpenes, diterpenes, sesquiterpenes, terpenoids, and terpene alcohols), esters, ethers, thiols, and aldehydes.

The term "harvest", is used herein with reference to the act of gathering a plant, or any physical part thereof.

The term "lipids", as used herein encompasses simple lipids and complex lipids, which include fatty acids, fatty acid subunits, n-alkanes and triglycerides.

The terms "method" and "process" may be used interchangeably herein with reference to a series of steps for accomplishing a result, e.g., a process for manufacturing a plant product.

The term, "organoleptic" is used with reference to acting on, or involving the use of, the sense organs.

The term, "Perfecto" is used with reference to a cigarette having a crutch, filter or tip at each end of the cigarette.

The term, "plant-associated chemical and biological ecology" as used herein includes carotenoids, phenols, anthocyanins, enzymes, resinoids, and the plant microbiome.

The term "plant material" is used herein with reference to freshly harvested parts of a plant. Examples include, but are not limited to, leaves, inflorescences (flowers), trichomes, needles, twigs, fruits, seeds, bark, and roots.

The term "plant type" is used with reference to a plant of a particular cultivar or having a particular chemotype. The terms "plant type" and "cultivar" may be used interchangeably herein.

The term "Quickie" is used herein with reference to a small cigarette contain less than 0.5 grams of plant material, e.g. 0.33 grams.

The term "powdered or liquid cannabinoids" as used herein includes crystalline THCa, cannabinoid isolates, and/or *Cannabis* distillates.

The term "pre-roll" or "preroll" is used with reference to prepared *Cannabis* cigarettes that consumers may purchase thereby avoiding the need to produce (roll) their own *Cannabis* cigarettes.

The term "sealer coating" is used herein with reference to an additive comprising a plant cellulose compound that may slow down off-gassing of low molecular weight compounds that contribute to flavor and fragrance.

The term "smokable product" is used herein with reference to cigarettes or similar articles that have a substantially cylindrical rod-shaped structure and include a charge, roll, or column of smokable material, such as a dried plant product, surrounded by a paper or plant-derived wrapper, to form a cigarette, "cigarette rod," or a "smokable rod". Tobacco is not a source of dried plant product.

The term "solventless extraction" is used herein with reference to extraction of an EOI resin using a non-hydrocarbon process, e.g., water, sieving, or other mechanical methods.

The terms "substrate", "plant substrate", "plant substrate material", and "plant material substrate" are used interchangeably herein with reference to dried plant material which may serve for attachment or trapping of an introduced EOI extract. While not wishing to be bound by theory, compounds separated from the plant's extracted resin, other lipid fractions, or polysaccharides may act as fixatives that are absorbed into or coat the dried substrate, facilitating the stability and reducing the volatility of light molecules, including monoterpenes and terpene alcohols.

The term "terpene" as used herein includes monoterpenes, diterpenes, sesquiterpenes, terpenoids, and terpene alcohols.

The term "THCa-reduced EOI extract" is used herein with reference to an EOI extract wherein the amount of THCa in the EOI extract has been reduced from about 75% to 80% or more to about 40 to 50%, 75% to 80% or more to about 35% to 45%, 75% to 80% or more to about 30% to 40%, 75% to 80% or more to about 70%, 65%, 60%, 55%, 50%, 45%, 40%, 35%, 30%, 25% or less. The THCa-reduced EOI extract may also be referred to as a high terpene EOI extract or a high terpene extract (HTE). In some embodiments, the THCa in a THCa-reduced EOI extract has been reduced by 10% or more, 15% or more, 20% or more, 25% or more, 30% or more, 35% or more, 40% or more, 50% or more, 55% or more, 60% or more, 65% or more, 70% or more, 75% or more, 80% or more, 85% or more, 90% or more, or 95%, or more. In some embodiments, a THCa-reduced EOI extract is made by extracting and crystallizing THCa.

The term "trichome" is used herein with reference to tiny glandular hairs that emerge from the surface of the buds, stalks, stems and leaves of plants including *Cannabis* plants. Under a microscope, trichomes look like mini mushrooms, comprised primarily of a stalk and a gland head, or just a gland head, and the gland head is where majority of the EOI resin resides. See, e.g., FIG. 1 of Smeriglio, et al., Molecules 2019, 24, 2941, which shows inflorescences of *Cannabis sativa* L showing stalked glandular trichomes with large heads where resin is produced and stored.

The term "vaporizable product" is used herein with reference to plant material that can be heated to temperatures below combustion, but above temperatures needed to liberate plant compounds in aerosol form for inhalation from the plant material.

Overview

The compositions and methods disclosed herein are based on the discovery that a fragrant and flavorful *Cannabis* plant product can be designed and produced that comprises a desired EOI that is broader, predictable and more stable than currently available. The EOI is extracted from one or more plant types and may be combined with dried plant material that serves as a substrate for the EOI extract with which it is combined. The EOI level for one or more EOI components in the plant products may be below, equal to, or exceed the EOI level of one or more EOI components in the living plant at the time of harvest. The plant products provide a customized EOI that may be used as an inhalable product. The processes described herein are used to design and create plant products with a novel, defined, and consistent EOI. The processes described herein may be used to create novel plant products that are not produced by any single cultivar or combination of cultivars.

Reference will now be made in detail to certain claims of the disclosure, examples of which are described and illustrated below. While the disclosure is described in conjunction with the enumerated claims, it will be understood that the disclosure is not intended to limit those claims. On the contrary, the disclosure is intended to cover all alternatives, modifications, and equivalents, which can be included within the scope of the disclosure as defined by the claims.
*Cannabis* Chemotypes.

*Cannabis* has been described as having particular chemotypes based on THCa, CBDA, CBGA, CBCA, their propyl cannabinoid and neutral cannabinoid variants, and terpene/terpenoid content.

For example, the term "Type I *Cannabis*", is used with reference to *Cannabis* plant material with a low CBDA/THCa ratio, typically due to a high THC content; the term "Type 11 *Cannabis*", is used with reference to *Cannabis* plant material which includes both of the two main cannabinoids, THCa and CBDA, in a content ratio close to the unity (typically ranging from 0.5 to 4.0); and the term "Type III *Cannabis*", is used herein with reference to *Cannabis* plant material has a high CBDA/THCa ratio, typically due to a high CBDA content, and an amount of THCa lower than 0.3%; and the term "Type IV *Cannabis*", is used herein with reference to *Cannabis* plant material has a high propyl cannabinoid content or ratios, typically due to a high propyl THCVA/CBDVA/CBGVA content in relation to pentyl cannabinoid content. See, e.g., de Meijer, E. et al. (2003) Genetics. 163(1):335-46.), and Hillig, K W et al., 2004, American Journal of Botany 91(6): 966-975.

Many cultivars of *Cannabis* are known in the art and many others are under development, however, it is virtually impossible to "dial-in" a formulation of choice and consistently produce it from a single cultivar. The methods and compositions described herein provide a solution. Disclosed herein are methods and compositions that provide a large number of *Cannabis* product formulations having defined chemistry and a known and consistent EOI.

In some embodiments, the disclosed fragrant and flavorful *Cannabis* plant products are made from a blend of flower and EOI extracts from one or more *Cannabis* cultivars. In some embodiments, the disclosed fragrant and flavorful *Cannabis* plant products are EOI extracts alone.

In some embodiments, the fragrant and flavorful *Cannabis* plant products are supplemented with supplemented with one or more fragrant and flavorful compounds, and one or more powered or liquid cannabinoids.

In some embodiments, the fragrant and flavorful *Cannabis* plant products are supplemented with one or more lipids, one or more fragrant and flavorful compounds, and one or more powered or liquid cannabinoids.

In some embodiments, the fragrant and flavorful *Cannabis* plant products are supplemented with one or more lipids, one or more fragrant and flavorful compounds, one or more powered or liquid cannabinoids and one or more components of the plant-associated chemical and biological ecology. By way of example, when four crosses were made between inbred *Cannabis sativa* plants with pure cannabidiol (CBD) and pure Delta-9-tetrahydrocannabinol (THC) chemotypes, all the plants belonging to the crosses were found to have a mixed CBD-THC chemotype. (See, de Meijer, E. et al. (2003) Genetics. 163(1):335-46.)

CBG has been shown to be the direct precursor of the cannabinoids CBD, THC and CBC. (See, de Meijer, E. & Hammond, K. (2005) Euphytica. 145. 189-198). Cannbigerolic acid (CBGA) is the substrate for THCA synthase, CBD synthase and CBC synthase. (See, e.g., FIG. 4 of Mandolino, G. and Carboni, A. (2004) Euphytica 140. 107-120.) It follows that a *Cannabis* cultivar lacking THC synthase will not produce THC, a *Cannabis* cultivar lacking CBD synthase will not produce CBD and a *Cannabis* cultivar lacking CBC synthase will not produce CBC. In addition, CBG does not form in a cultivar lacking geranyl diphosphate:olivetolate geranyl transferase (GOT), which catalyzes the condensation of geranygeraniol diphosphate with olivetolic acid. (See, e.g., Staginnus, C, Zorntlein, S., de Meijer, E. (2014) J Forensic Sci. 59(4): 919-26.)

In addition, a cannabinoid-free *Cannabis sativa* chemotype has been described where the composition of terpenes and other compound classes remained unaffected. (See, de Meijer, E. & Hammond, K. M. & Sutton, A. (2009) Euphytica. 168. 95-112.)

Propyl and pentyl cannabinoids have been studied and the pentyl chemotype, i.e., CBG-derived cannabinoids: THC, CBD and CBC, has been demonstrated to be the most common. Propyl cannabinoids include CBGV-derived cannabinoids, THCV, CBDV, and CBCV are also found in numerous *Cannabis* cultivars. (See, e.g., de Meijer, E. & Hammond, K. (2016) Euphytica, 210. 291-307.)

Plant material from *Cannabis* cultivars exhibiting any of the above-referenced characteristics may be used in methods and compositions described herein.

With respect to terpene content, the following essential oil superclasses have been identified: Caryophyllene, Limonene, Myrcene, Ocimene, Terpinolene, Linalool, and Pinene superclasses, each of which includes subclasses. Table 1 provides a listing of exemplary *Cannabis* varieties characterized in terms of terpene content and terpene superclass and subclass.

TABLE 1

| Terpene Superclasses. TERPENE SUPERCLASSES | | |
| --- | --- | --- |
| Dominant terpenes | Secondary characteristics | Cultivar examples - vernacular names |
| Terpinolene | alpha- & beta-phellandrene, 3-carene, alpha-terpinene | Jack Herer, Trainwreck, S.A.G.E., Big Sur Holy, Durban Poison |
| β-Caryophyllene, alcohol-substituted terpenoids | limonene:humulene 1:1 | Cookies family |
| | limonene:humulene 2:1 | Sherbert |
| | limonene:myrcene 1:1 | Gorilla Glue #4 |

TABLE 1-continued

Terpene Superclasses.
TERPENE SUPERCLASSES

| Dominant terpenes | Secondary characteristics | Cultivar examples - vernacular names |
|---|---|---|
| Limonene/myrcene-dominant, alcohol-substituted terpenoid s | limonene:myrcene 1:1 | OG Kush, Skywalker OG, Louis XIII, Tahoe OG, Wifi |
| | limonene:myrcene 2:1 limonene:linalool 3:1 | Miami White Kush, Triple O, Headband Gelato |
| Limonene/myrcene/beta-caryophyllene-dominant, bisabolol | limonene: beta-caryophyllene: myrcene 2:2:1 | Bubba Kush, Master Kush |
| | limonene:myrcene:beta-caryophyllene:1:1:1 | Mr. Nice |
| Myrcene-dominant | alpha-pinene > trans-ocimene | Mendo Purps, Grape Ape, Purple Cream, Grandaddy Purple, Purple Urkle |
| | alpha-pinene:beta-pinene 2:1 | Blue Dream, Blueberry Haze |
| | trans-ocimene > limonene | Strawberry Cough |
| | trans-ocimene = limonene | Pincher Creek, Green Crack |
| | alpha-pinene > limonene | AK-47, Godfather |
| Linalool-dominant | linalool:limonene | Lavender |

See, e.g., Backes, Michael, *Cannabis* Pharmacy: The Practical Guide to Medical Marijuana, Black Dog and Levanthal Publishers, 2017; Lewis, Mark A. et al., Planta Medica 84.04 (2018): 225-233; and Fischedick, Justin T., *Cannabis* and Cannabinoid Research 2.1 (2017): 34-47.

Examples of the terpene profile of 3 marijuana cultivars (OG Kush, Bubba Kush and Sour Diesel) in the most common terpene subclass, LCM (limonene, caryophyllene, myrcene), are shown in Table 2, which also illustrates the terpene profile of a variety of *Cannabis* cultivars with different terpenoid profiles.

α-gurjunene, santolina triene, sesquiterp-1, δ-cadinene; Group 3 (herbal, woody, floral, citrus) α-amorphene, caryophyllene oxide, germacrene B, γ-elemene, 2-carene, (Z,Z)-α-farnesene, α-cubenene, β-elemene, β-sesquiphellandrene; Group 4 (citrus, woody, sweet, spicy) α-thujene, α-terpinene, cis-β-terpineol, α-santalene, α-bulnesene, α-fenchene, cis-β-farnesene, p-cymene, α-phellandrene, γ-terpinene, terpinolene, linalool, δ-selinene, 3-carene, α-eudesmol, terpinen-4-ol, p-cymenene, β-phellandrene, bulnesol; and Group 5 (citrus, woody, sweet, tropical)

TABLE 2

Results of Terpene Analysis of Exemplary Cannabis Cultivars.

| Name | OG Kush | Bubba Kush | Sour Diesel | Oakland Kryptonite | Mendocino Purps | Blue Dream | NL5 × Haze | Cookies/ GG4 | Most Type II CBD* |
|---|---|---|---|---|---|---|---|---|---|
| α-Pinene | 0.04% | 0.03% | 0.03% | 0.07% | 0.29% | 0.21% | 0.40% | 0.03% | 0.36% |
| β-Pinene | 0.09% | 0.07% | 0.05% | 0.11% | 0.07% | 0.09% | 0.12% | 0.06% | 0.18% |
| β-Myrcene | 0.70% | 0.15% | 0.18% | 0.10% | 0.60% | 0.49% | 0.51% | 0.17% | 1.36% |
| α-Phellandrene | | | | | | | | | |
| Limonene | 0.47% | 0.39% | 0.34% | 0.66% | 0.03% | 0.07% | 0.06% | 0.35% | 0.19% |
| β-Ocimene | | | | 0.04% | 0.09% | | 0.02% | | |
| Terpinolene | 0.01% | | | 0.01% | | | | | |
| Linalool | 0.14% | 0.18% | 0.16% | 0.04% | 0.11% | 0.03% | 0.04% | 0.23% | 0.13% |
| Fenchol | 0.05% | 0.05% | 0.03% | 0.05% | | 0.01% | | 0.04% | 0.02% |
| (-)-Isopulegol | | | | | | | | | |
| α-Terpineol | 0.06% | 0.05% | 0.03% | 0.06% | | 0.01% | 0.01% | 0.04% | 0.08% |
| β-Caryophyllene | 0.66% | 0.39% | 0.36% | 0.85% | 0.44% | 0.12% | 0.24% | 0.97% | 0.26% |
| α-Humulene | 0.19% | 0.10% | 0.10% | 0.20% | 0.11% | | 0.09% | 0.45% | 0.18% |
| Caryophyllene Oxide | 0.02% | 0.01% | | 0.01% | 0.01% | | | 0.01% | |
| Camphene | 0.01% | 0.01% | | 0.01% | | | | 0.01% | 0.01% |

*e.g., (Charlotte's Web, ACDC, Cannatonic)

Mudge et al., Planta Med 2019; 85(09/10): 781-796, present an extensive list of terpenes characterized by aroma, as follows: Group 1 (woody, pine, citrus, spicy, floral) α-pinene, β-pinene, trans-2-pinanol, camphene, α-gurjunene derivative, β-maaliene, selina-3,7(11)-diene, camphene hydrate, α-bergamotene, 4,11-selinadiene, endoborneol, fenchone, Z-sabinene hydrate, γ-gurjunene, β-myrcene, caryophyllene, copaene, γ-muurolene, D-limonene, α-terpineol, β-cubebene, valencene, guaia-3,9-diene, germacrene A, ylangene, humulene, α-selinene, exofenchol, β-selinene; Group 2 (floral, woody, herbal)

alloaromadendrene, guaiol, 10-epi-γ-eudesmol, cis-α-bisabolene, cis-β-ocimene, trans-β-ocimene, sabinene.

Henry, Philipp, peerj.com/preprints/3307v1 presents categories of terpene hyperclasses and subclasses for 33 *Cannabis* accessions based on genetic analysis using snps. See, also Smeriglio, et al., Molecules 2019, 24, 2941, which presents the results of hydrodistillation of the aerial parts of *C. sativa* which resulted in an essential oil yield of 0.2% (v/w), and included the identification of 79 compounds of the following types, 0.51% monoterpene hydrocarbons, 0.52% oxygenated monoterpenes, 52.26% sesquiterpene hydrocarbons, 4.87% oxygenated sesquiterpenes, 1.24% cannabinoids, and 0.6% other compounds.

Entourage of Interest (EOI)

In some embodiments, the EOI includes one or more cannabinoids, fragrant and flavorful compounds (terpenes, terpenoids, terpene alcohols, esters, ethers, thiols, and aldehydes) flavonoids, carotenoids, phenols, anthocyanins, enzymes, microbiome, lipids, and resinoids.

Cannabinoids that may be present in an EOI include pentyl and propyl cannabinoid acids produced by the plant, e.g., THCA (Δ9-tetrahydrocannabinolic acid), CBDA (Cannabidiolic acid), CBCA (Cannabichromenenic acid), CBGVA (Cannabigerovarinic acid), THCVA (Tetrahydrocanabivarinic acid), CBDVA (Cannabidivarinic acid), CBCVA (Cannabichromevarinic acid) and CBGA (Cannabigerolic acid), and the corresponding cannabinoid compounds that are produced following decarboxylation, THC ($\Delta^9$-tetrahydrocannabinol), CBD (Cannabidiol), CBC (Cannabichromene), CBGV (Cannabigerivarin), THCV (Tetrahydrocannabivarin), CBDV (Cannabidivarin), CBCV (Cannabichromevarin), and CBG (Cannabigerol).

In some embodiments, the fresh plant material at the time of harvest comprises a total cannabinoid content of from about 0.1% to 8.0%, 0.2% to 7.5%, 0.3% to 7.0%, 0.4% to 6.5%, 0.5% to 6.0%, 0.6% to 5.5%, 0.7% to 5.0%, 0.8% to 4.5%, 0.9% to 4.0%, 1.0% to 3.5%, 1.5% to 3.0%, or from 2.0% to 2.5% by weight, wherein the cannabinoids may include one or more of THCa, THCVa, Δ9-THC, Δ8-THC, THCV, CBDa, CBD, CBDVa, CBDV, CBN, CBGVa, CBGa, CBGV, CBG, CBCVa, CBCV, CBCa, and CBC.

In some embodiments, the fresh plant material at the time of harvest comprises a total cannabinoid content of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, or about 9.0% by weight.

In some embodiments, dried plant material substrate comprises a total cannabinoid content of from about 0.3% to 45.0% or more by weight wherein the cannabinoids may include one or more of THCa, THCVa, Δ9-THC, Δ8-THC, THCV, CBDa, CBD, CBDVa, CBDV, CBN, CBGVa, CBGa, CBGV, CBG, CBCVa, CBCV, CBCa, and CBC.

In some embodiments, dried plant material substrate comprises a total cannabinoid content of from about 1% to 45%, 5% to 35%, 10% to 30%, or about 15% to 25% by weight, for example, about 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, or about 45.0% by weight.

In some embodiments, the EOI extract comprises a total cannabinoid content of from about 0.1% to 80% wherein the cannabinoids may include one or more of THCa, THCVa, Δ9-THC, Δ8-THC, THCV, CBDa, CBD, CBDVa, CBDV, CBN, CBGVa, CBGa, CBGV, CBG, CBCVa, CBCV, CBCa, and CBC.

In some embodiments, the EOI extract comprises a total cannabinoid content of from about 0.1% to 80%, 1% to 75%, 5% to 70%, 10% to 65%, 15% to 60%, 20% to 55%, 25% to 50%, 30% to 45%, 35% to 50%, 40% to 45%, or from about 3.5% to 6% by weight, for example, about 0.1%, 0.2%, 0.3%, 0.4%, 0.5%, 0.6%, 0.7%, 0.8, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7, 2.8%, 2.9%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, 50.0%, 50.5%, 51.0%, 51.5%, 52.0%, 52.5%, 53.0%, 53.5%, 54.0%, 54.5%, 55.0%, 55.5%, 56.0%, 56.5%, 57.0%, 57.5%, 58.0%, 58.5%, 59.0%, 59.5%, 60.0%, 60.5%, 61.0%, 61.5%, 62.0%, 62.5%, 63.0%, 63.5%, 64.0%, 64.5%, 65.0%, 65.5%, 66.0%, 66.5%, 67.0%, 67.5%, 68.0%, 68.5%, 69.0%, 69.5%, 70.0%, 70.5%, 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, or about 80.0% by weight. In some embodiments, the final plant product comprises a total cannabinoid content of from about 0.1 to 45% by weight wherein the cannabinoids may include one or more of THCa, THCVa, Δ9-THC, Δ8-THC, THCV, CBDa, CBD, CBDVa, CBDV, CBN, CBGVa, CBGa, CBGV, CBG, CBCVa, CBCV, CBCa, and CBC.

In some embodiments, the final *Cannabis* plant product comprises a total cannabinoid content of from about 0.1% to 45%, 1% to 40%, 5% to 35%, 10% to 30%, or about 15% to 25% by weight, for example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0%, 14.5%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29.0%, 29.5%, 30.0%, 30.5%, 31.0%, 31.5%, 32.0%, 32.5%, 33.0%, 33.5%, 34.0%, 34.5%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, or about 45.0% by weight.

In some embodiments, the fresh plant material at the time of harvest comprises a total THC (THCa+THC) to total CBD (CBDA+CBD) ratio of from about 1 to 25 or from about 25 to 1.

In some embodiments, the fresh plant material at the time of harvest comprises a total THC (THCa+THC) to total CBD (CBDA+CBD) ratio of from about 1:1, 1:2, 1:3, 1:4, 1:5, 1:6, 1:7, 1:8, 1:9, 1:10, 1:11, 1:12, 1:13, 1:14, 1:15, 1:16, 1:17, 1.18, 1:19, 1:20, 1:21, 1:22, 1:23, 1:24, 1:25, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, or 3:1, or about 2:1.

In some embodiments, the dried plant material substrate comprises a total THC (THCa+THC) to total CBD (CBDA+CBD) ratio of from about 1 to 110 or from about 110 to 1.

In some embodiments, the EOI extract comprises a total THC (THCa+THC) to total CBD (CBDA+CBD) ratio of from about 1 to 200 or from about 200 to 1.

In some embodiments, the final plant product comprises a total THC (THCa+THC) to total CBD (CBDA+CBD) ratio of from about 1 to 200 or from about 200 to 1.

In some embodiments, the dried plant material substrate, the EOI extract and/or the final plant product may comprises a total THC (THCa+THC) to total CBD (CBDA+CBD) ratio of from about 1:200 to 200:1, 1:1 to 1:2, 1:2 to 1:4, 1:4 to 1:8, 1:8 to 1:18, 1:18 to 1:25, 1:25 to 1:50, 1:50 to 1:80, 1:80 to 1:110, 1:110 to 1:140, 1:140 to 1:170, 1:170 to 1:200, 200:1 to 170:1, 170:1 to 140:1, 140:1 to 110:1, 110:1 to 80:1, 80:1 to 50:1, 50:1 to 25:1, 25:1 to 18:1, 18:1 to 8:1, 8:1 to 4:1, or from about 4:1 to 2:1, for example, about 1:1, 1:2, 1:3, 1:4, 1:5, 1:6, 1:7, 1:8, 1:9, 1:10, 1:11, 1:12, 1:13, 1:14, 1:15, 1:16, 1:17, 1.18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, 1:55, 1:56, 1:57, 1:58, 1:59, 1:60, 1:61, 1:62, 1:63, 1:64, 1:65, 1:66, 1:67, 1:68, 1:69, 1:70, 1:71, 1:72, 1:73, 1:74, 1:75, 1:76, 1:77, 1:78, 1:79, 1:80, 1:81, 1:82, 1:83, 1:84, 1:85, 1:86, 1:87, 1:88, 1:89, 1:90, 1:91, 1:92, 1:93, 1:94, 1:95, 1:96, 1:97, 1:98, 1:99, 1:100, 1:101, 1:102, 1:103, 1:104, 1:105, 1:106, 1:107, 1:108, 1:109, 1:110, 1:100, 1:101, 1:102, 1:103, 1:104, 1:105, 1:106, 1:107, 1:108, 1:109, 1:110, 1:111, 1:112, 1:113, 1:114, 1:115, 1:116, 1:117, 1:118, 1:119, 1:120, 1:121, 1:122, 1:123, 1:124, 1:125, 1:126, 1:127, 1:128, 1:129, 1:130, 1:131, 1:132, 1:133, 1:134, 1:135, 1:136, 1:137, 1:138, 1:139, 1:140, 1:141, 1:142, 1:143, 1:144, 1:145, 1:146, 1:147, 1:148, 1:149, 1:150, 1:151, 1:152, 1:153, 1:154, 1:155, 1:156, 1:157, 1:158, 1:159, 1:160, 1:161, 1:162, 1:163, 1:164, 1:165, 1:166, 1:167, 1:168, 1:169, 1:170, 1:171, 1:172, 1:173, 1:174, 1:175, 1:176, 1:177, 1:178, 1:179, 1:180, 1:181, 1:182, 1:183, 1:184, 1:185, 1:186, 1:187, 1:188, 1:189, 1:190, 1:191, 1:192, 1:193, 1:194, 1:195, 1:196, 1:197, 1:198, 1:199, 1:200, 200:1, 199:1, 198:1, 197:1, 196:1, 195:1, 194:1, 193:1, 192:1, 191:1, 190:1, 189:1, 188:1, 187:1, 186:1, 185:1, 184:1, 183:1, 182:1, 181:1, 180:1, 179:1, 178:1, 177:1, 176:1, 175:1, 174:1, 173:1, 172:1, 171:1, 170:1, 169:1, 168:1, 167:1, 166:1, 165:1, 164:1, 163:1, 162:1, 161:1, 160:1, 159:1, 158:1, 157:1, 156:1, 155:1, 154:1, 153:1, 152:1, 151:1, 150:1, 149:1, 148:1, 147:1, 146:1, 145:1, 144:1, 143:1, 142:1, 141:1, 140:1, 139:1, 138:1, 137:1, 136:1, 135:1, 134:1, 133:1, 132:1, 131:1, 130:1, 129:1, 128:1, 127:1, 126:1, 125:1, 124:1, 123:1, 122:1, 121:1, 120:1, 119:1, 118:1, 117:1, 116:1, 115:1, 114:1, 113:1, 112:1, 111:1, 110:1, 109:1, 108:1, 107:1, 106:1, 105:1, 104:1, 103:1, 102:1, 101:1, 100:1, 99:1, 98:1, 97:1, 96:1, 95:1, 94:1, 93:1, 92:1, 91:1, 90:1, 89:1, 88:1, 87:1, 86:1, 85:1, 84:1, 83:1, 82:1, 81:1, 80:1, 79:1, 78:1, 77:1, 76:1, 75:1, 74:1, 73:1, 72:1, 71:1, 70:1, 69:1, 68:1, 67:1, 66:1, 65:1, 64:1, 63:1, 62:1, 61:1, 60:1, 59:1, 58:1, 57:1, 56:1, 55:1, 54:1, 53:1, 52:1, 51:1, 50:1, 49:1, 48:1, 44:1, 46:1, 45:1, 44:1, 43:1, 42:1, 41:1, 40:1, 39:1, 38:1, 37:1, 36:1, 35:1, 34:1, 33:1, 32:1, 31:1, 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, or 3:1, or 2 about 2:1.

Terpenes that may be present in a selected EOI include but are not limited to, β-caryophyllene, β-myrcene, γ-limonene, linalool, α-humulene, β-pinene, α-pinene, α-bisabolol, α-terpinene, β-ocimene, camphene, caryophyllene oxide, cis-nerolidol, γ-3-carene, eucalyptol, γ-terpinene, geraniol, ocimene, (−)-guaiol, (−)-isopulegol, p-cymene, terpinolene, trans-nerolidol, gerol, geranyl acetate, α-terpineol, α-phellanderene, sabinene, thymol, cedrene, cedrol, fenchol, valencene, α-thujene, and cymene. This includes diterpenes, such as phytol, steviol glycosides, retinol, and retinal; sesquiterpenes such as β-caryophyllene, α-humulene, and nootkatone; and tetraterpenes such as α-carotene, β-carotene, gamma-carotene, lycopene, lutein, zeaxanthin, neoxanthin, violaxanthin, flavoxanthin, α-cryptoxanthin, and β-cryptoxanthin, and the Group 1-5 terpenes described by Mudge et al., Planta Med 2019; 85(09/10): 781-796, listed above.

In some embodiments, the fresh plant material at the time of harvest comprises a total terpene content of from about 0.1% to 1.0%, 0.2% to 1.1%, 0.3% to 1.2%, 0.4% to 1.3%, 0.5% to 1.5%, 0.6% to 1.6%, 0.7 to 1.5%, 0.8 to 1.4%, 0.9 to 1.3%, or from about 1.0 to 1.2%, for example, about 0.6%, 0.7%, 0.8%, 0.9%, 1.0%, 1.1%, 1.2%, 1.3%, 1.4%, 1.5%, or about 1.6% by weight, wherein the terpenes include one or more of β-caryophyllene, β-myrcene, limonene, linalool, α-humulene, β-pinene, α-pinene, α-bisabolol, α-terpinene, β-ocimene, camphene, caryophyllene oxide, cis-nerolidol, γ-3-carene, eucalyptol, γ-terpinene, geraniol, ocimene, (−)-guaiol, (−)-isopulegol, p-cymene, terpinolene, trans-nerolidol, gerol, geranyl acetate, α-terpineol, α-phellanderene, sabinene, thymol, cedrene, cedrol, fenchol, valencene, α-thujene, cymene and the Group 1-5 terpenes described by Mudge et al., Planta Med 2019; 85(09/10): 781-796, listed above.

In some embodiments, the dried plant material substrate comprises a total terpene content of from about 0.1% to 8.0%, 0.15% to 7.5%, 0.2% to 7.0%, 0.3% to 6.0%, 0.4% to 5.5%, 0.5% to 5.0%, 0.6% to 4.5%, 0.7% to 4.0%, 0.8% to 3.5%, 0.9% to 3.0%, 1.0% to 3.5%, or from about 1.5% to 3.0%, for example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.1%, 7.2%, 7.3%, 7.4%, 7.5%, 7.6%, 7.7%, 7.8%, 7.9%, or about 8.0%, wherein the terpenes include one or more of β-caryophyllene, β-myrcene, limonene, linalool, α-humulene, β-pinene, α-pinene, α-bisabolol, α-terpinene, β-ocimene, camphene, caryophyllene oxide, cis-nerolidol, γ-3-carene, eucalyptol, γ-terpinene, geraniol, ocimene, (−)-guaiol, (−)-isopulegol, p-cymene, terpinolene, trans-nerolidol, gerol, geranyl acetate, α-terpineol, α-phellanderene, sabinene, thymol, cedrene, cedrol, fenchol, valencene, α-thujene, cymene and the Group 1-5 terpenes described by Mudge et al., Planta Med 2019; 85(09/10): 781-796, listed above.

In some embodiments, the EOI extract comprises a total terpene content of from about 5% to 75%, 10% to 75%, 15% to 70%, 20% to 60%, 25% to 55%, 30% to 50%, or from about 35% to 45%, for example, about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or about 75%, wherein the terpene content includes one or more of β-caryophyllene, β-myrcene, limonene, linalool, α-humulene, β-pinene, α-pinene, α-bisabolol, α-terpinene, β-ocimene, camphene, caryophyllene oxide, cis-nerolidol, γ-3-carene, eucalyptol, γ-terpinene, geraniol, ocimene, (−)-guaiol, (−)-isopulegol, p-cymene, terpinolene, trans-nerolidol, gerol, geranyl acetate, α-terpineol, α-phellanderene, sabinene, thymol, cedrene, cedrol, fenchol, valencene, α-thujene, cymene and the Group 1-5 terpenes described by Mudge et al., Planta Med 2019; 85(09/10): 781-796, listed above.

In some embodiments, the final fragrant and flavorful *Cannabis* plant product comprises a total terpene content of from about 0.5 to 25%, 0.5% to 20%, 0.5% to 15%, 0.5% to 10%, 0.5% to 5%, 1% to 15%, 1% to 10%, 1% to 5%, 1.5% to 10%, 2% to 8%, 2.5% to 6%, 2.75% to 5%, 3% to 4.5%, 3.25% to 4.25%, 3.5% to 4%, or from about 3% to 3.75%, for example, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10.0%, 10.1%, 10.2%, 10.3%, 10.4%, 10.5%, 10.6%, 10.7%, 10.8%, 10.9%, 11.0%, 11.1%, 11.2%, 11.3%, 11.4%, 11.5%, 11.6%, 11.7%, 11.8%, 11.9%, 12.0%, 12.1%, 12.2%, 12.3%, 12.4%, 12.5%, 12.6%, 12.7%, 12.8%, 12.9%, 13.0%, 13.1%, 13.2%, 13.3%, 13.4%, 13.5%, 13.6%, 13.7%, 13.8%, 13.9%, 14%, 14.1%, 14.2%, 14.3%, 14.4%, 14.5%, 14.6%, 14.7%, 14.8%, 14.9%, 15.0%, 15.0% to 16.0%, 16.0% to 17.0%, 17.0% to 18.0%, 18.0% to 19.0%, 19.0% to 20.0%, 20.0%, to 21.0%, 21.0% to 22.0%, 22.0% to 23.0%, 23.0% to 24.0%, 24.0% to 25.0%, wherein the terpenes include one or more of β-caryophyllene, β-myrcene, limonene, linalool, α-humulene, β-pinene, α-pinene, α-bisabolol, α-terpinene, β-ocimene, camphene, caryophyllene oxide, cis-nerolidol, γ-3-carene, eucalyptol, γ-terpinene, geraniol, ocimene, (−)-guaiol, (−)-isopulegol, p-cymene, terpinolene, trans-nerolidol, gerol, geranyl acetate, α-terpineol, α-phellanderene, sabinene, thymol, cedrene, cedrol, fenchol, valencene, α-thujene, cymene and the Group 1-5 terpenes described by Mudge et al., Planta Med 2019; 85(09/10): 781-796, listed above.

In some embodiments, the final plant product comprises a monoterpenes content of 1% to 10%, at least 2%, at least 2.5%, at least 3%, at least 3.5%, at least 4%, at least 4.5%, at least 5%, at least 5.5%, at least 6%, at least 6.5%, at least 6%, at least 6.5%, at least 7%, at least 7.5%, at least 8%, at least 8.5%, at least 9%, at least 9.5%, or at least 10%, e.g., 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0%.

In some embodiments, the final plant product comprises a low sesquiterpene content of from about 0% to about 2.0%, from 0% to about 1.5%, from about 0% to about 1.0%, from 0% to about 0.5%, from about 0.2% to about 1.0%, from 0.2% to about 0.8%, from 0.2% to about 0.7%, from 0.2% to about 0.6%, from 0.2% to about 0.5%, for example, less than 2.0%, less than 1.8%, less than 1.6%, less than 1.4%, less than 1.2%, less than 1.0%, less than 0.8%, less than 0.7%, less than 0.6%, or less than 0.5%. less than 0.4%, less than 0.3%, or less than 0.2%. It will be understood by those of skill in the art that a low sesquiterpene content reduces impairment side effects.

In some embodiments, the EOI extract comprises one or more of the following: 7,8-dihydroionone, acetanisole, acetic acid, acetyl cedrene, anethole, anisole, benzaldehyde, bergamotene (c-cis-bergamotene), (c-trans-bergamotene), bisabolol (e.g., β-bisabolol), borneol, bornyl acetate, butanoic/butyric acid, cadinene (c-cadinene), (γ-cadinene), cafestol, caffeic acid, camphene, camphor, capsaicin, carene (a-3-carene), carotene, carvacrol, carvone, dextro-carvone, laevo-carvone, caryophyllene (e.g., β-caryophyllene), caryophyllene oxide, castoreum absolute, cedrene (c.-cedrene), (β-cedrene), cedrene epoxide, (c-cedrene epoxide), cedrol, cembrene, chlorogenic acid, cinnamaldehyde (c-amyl-cinnamaldehyde), (c-hexyl-cinnamaldehyde), cinnamic acid, cinnamyl alcohol, citronelal, citronelol, cryptone, curcumene, (c-curcumene), (γ-curcumene), decanal, dehydrovomifoliol, dialyl disulfide, dihydroactinidiolide, dimethyl disulfide, eicosane/icosane, elemene (b-elemene), estragole, ethyl acetate, ethyl cinnamate, ethylmaltol, eucalyptol/1.8-cineole, eudesmol (c-eudesmol), (b-eudesmol), (γ-eudesmol), eugenol, euphol, farnesene, farnesol, fenchol (b-fenchol), fenchone, geraniol, geranylacetate, germacrenes, germacreneb, guaia-1(10), 1-diene, guaiacol, guaiene (c-guaiene), gurunene (c-gurunene), herniarin, hexanaldehyde, hexanoic acid, hexyl butyrate, humulene (c.-humulene), (β-humulene), ionol (3-oxo-c.-ionol) (b-ionol), ionone(c-ionone)(b-ionone), ipsdienol, isoamyl acetate, isoamyl alcohol, isoamyl formate, isoborneol, isomyrcenol, isopulegol, isovalericacid, isoprene, kahweol, lavandulol, limonene, γ-linolenic acid, linalool, longifolene, c-longipinene, lycopene, menthol, methylbutyrate, 3-mercapto-2-methylpentanal, mercaptan/thiols, β-mercaptoethanol, mercaptoacetic acid, alyl mercaptan, benzyl mercaptan, butyl mercaptan, ethyl mercaptan, methyl mercaptan, furfuryl mercaptan, ethylene mercaptan, propyl mercaptan, thenyl mercaptan, methyl salicylate, methylbutenol, methyl-2-methylvalerate, methyl thiobutyrate, myrcene (β-myrcene), γ-muurolene, nepeta lactone, nerol, nerolidol, nerylacetate. nonanaldehyde, nonanoic acid, ocimene, octanal, octanoic acid, p-cymene, penty-1-butyrate, phelandrene, phenylacetaldehyde, phenylethanethiol, phenylacetic acid, phytol, α-pinene, β-pinene, propanethiol, pristimerin, pulegone, quercetin, retinol, rutin, sabinene, sabinene hydrate, cis-sabinene hydrate, trans-sabinene hydrate, safranal, c-selinene, c-sinensal, b-sinensal, b-sitosterol, squalene, taxadiene, terpin hydrate, terpineol, terpine-4-ol, c-terpinene, γ-terpinene, terpinolene, thiophenol, α-thujene, thujone, thymol, c-tocopherol, undecanone, undecanal, valeraldehyde/pentanal, verdoxan, c-ylangene, umbelliferone, vanillin, citronellol, eremanthine, 15-methoxypinusolidic acid, ajugalide, carnosol, triptolide, asiatic acid, thymoquinone, bilobalide, isoatriplicolide tiglate, tanshinone IIA, deoxygedunin and obacunone. In some embodiments, such EOI components are in the form of c-, 3-, y-, oxo-isomers, or combinations thereof.

In many embodiments a formulation having defined chemistry is developed and produced such that the fragrant and flavorful *Cannabis* plant product includes specific components in defined amounts, wherein the amount of each component varies by 0 to 10%. The amount of a given component in a formulation having defined chemistry may vary by 0%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, or 10.0% by weight.

In some embodiments, the EOI extract (resin) is expelled or extracted from plant material other than inflorescences, and may include one or more of apigenin, anthocyanin, β-sitosterol, campesterol, cannflavin A, cannflavin B, carotene, ergosterol, phloroglucinol glucoside, stigmasterol, and xanthophylls.

In some embodiments, the EOI extract (resin) is treated to remove THCa, e.g., at least 10%, 15%, 20%, 25%, 30%, 35%, 40%, 45%, 50%, 55%, 60%, 65%, 70%, 75%, 80%, 85%, 90%, 95%, or 100% of the THCa in the EOI resin is removed.

In some embodiments, the EOI resin is expelled or extracted from *Cannabis* (marijuana) plant material to yield an EOI extract.

In some embodiments, the EOI resin is expelled or extracted from hemp plant material to yield an EOI extract.

In some embodiments, an EOI extract is mixed with plant material substrate from one or more types of *Cannabis* (marijuana) plants.

In some embodiments, an EOI extract is mixed with plant material substrate from one or more types of hemp plants.

In some embodiments, the EOI resin is expelled or extracted from non-*Cannabis* plant material.

In some embodiments, EOI components noted above are expelled or extracted from an EOI resin using a solventless process and included in the EOI extract used in the methods disclosed herein to make a plant product.

In some embodiments, EOI components listed above are extracted from an EOI resin using a hydrocarbon solvent and included in the EOI extract used in the methods disclosed herein to make a fragrant and flavorful *Cannabis* plant product.

In some embodiments, the desired EOI is obtained from one plant cultivar or plants with a particular chemotype.

In some embodiments, an EOI extract is mixed with a plant material substrate of the same plant type to produce the plant product.

In some embodiments, an EOI extract is mixed with plant material substrate from one or more different plant types to produce the plant product.

In some embodiments, one or more EOI extracts are formulated from plant material harvested from more than one plant type that may or may not be a cultivated plant.

In some embodiments, EOI extracts are formulated by blending, then mixed with plant material substrate to produce the plant product.

In some embodiments, EOI extracts are supplemented with one or more additional terpenes and/or cannabinoids to yield a formulation that contains the desired EOI.

In some embodiments, a plant material substrate is selected for greater binding of terpenes (monoterpenes, diterpenes, sesquiterpenes, terpenoids, and terpene alcohols), esters, ethers, thiols and aldehydes, as compared to other plant material substrates.

In some embodiments, a plant material substrate is selected for its ability to reduce the degradation and/or volatilization of terpenes (monoterpenes, diterpenes, sesquiterpenes, terpenoids, and terpene alcohols), esters, ethers, thiols and aldehydes, as compared to other plant material substrates.

Analytics

Analyses may be carried out on one or more, or all of the plant material and plant material extracts described herein. The analysis may be chemical analysis and/or genetic analysis.

In the processes disclosed herein, the EOI of fresh plant material may be analyzed at the time of harvest for selected compounds including cannabinoids, terpenes (monoterpenes, diterpenes, sesquiterpenes, terpenoids, and terpene alcohols), esters, ethers, thiols and aldehydes. In some embodiments, analysis of one or more, or all of the (a) pre-harvest plant material, (b) post-harvest EOI extract, (c) post-harvest dried plant substrate material, (d) post-harvest dried and chopped plant substrate material, and (e) final plant product, is carried out using any of a number of analytical methods, for example, a standard *Cannabis* testing package available from any of a number of commercial labs. The standard *Cannabis* testing package typically includes an analysis of common cannabinoids and terpenes. Such a standard *Cannabis* testing package may be supplemented with analysis of additional compounds of interest. In some cases, genetic analysis of plant material may be carried out, for example, by testing for (a) specific snps, genetic markers or genetic sequences, (b) genes, (c) sequencing of the entire genome, or (d) RNA analysis for gene expression.

In some embodiments, a chemical testing package provides the results of a quantitative analysis of cannabinoids including, but not limited to, THCa, THCVa, Δ9-THC, Δ8-THC, THCV, CBDa, CBD, CBDVa, CBDV, CBN, CBGVa, CBGa, CBGV, CBG, CBCVa, CBCV, CBCa, and CBC. In some embodiments, additional cannabinoids are analyzed.

In some embodiments, the chemical testing package provides the results of a quantitative analysis of terpenes including, but not limited to, terpinolene, α-phellandrene, β-ocimene, carene, limonene, γ-terpinene, α-pinene, α-terpinene, β-pinene, fenchol, camphene, α-terpineol, α-humulene, β-caryophyllene, linalool, caryophyllene oxide, and myrcene.

In some embodiments, the chemical testing package provides a quantitative analysis of terpenes including, but not limited to, α-Pinene, b-Pinene, b-Myrcene, α-Phellandrine, Limonene, b-Ocimene, Terpinolene, Linalool, Fenchol, (−)-Isopulegol, α-Terpineol, b-Caryophyllene, α-Humulene, Valencene, Nerolidol, Caryophyllene Oxide, Guaiol, α-Bisabolol, Camphene, Geraniol, Eucalyptol, Cedrol, Geranyl Acetate, Cedrene, Sabinene, Camphor, Isobormeol, Bormeol, Menthol, Nerol, R-(+)-Pulgone, Terpinene, Sabiene hydrate, Fenchone, 3-Carene, α-Terpinene. In some embodiments, additional terpenes are analyzed.

Selecting Plants

Historically, the overall quality of a plant product, for example, an inhalable or smokable plant product ultimately depends on the plant or plants from which it is derived. In other words, the source material that was extracted defined the ceiling of the EOI. The current disclosure is directed to the surprising and unexpected discovery that fresh plant material can be processed in a manner to generate a stable and consistent plant product with a selected EOI designed to match the EOI desired by consumers, where the source material that is extracted does not define the ceiling of the EOI.

Plant Types.

In some embodiments, fresh plant material is obtained from a cultivated or wild-type plant. The plant may have: (a) an EOI of interest; (b) one or more differing levels of components of an EOI of interest; (c) desirable growth properties; (d) a known chemotype; (e) stable genetics; (f) pest resistance, or (g) a novel or uncommon genotype or chemotype.

In some embodiments, fresh plant material is obtained from more than one plant, for example, (a) from different chemotypes of the same cultivar; (b) from different genera or species of plants; (c) from plants having different chemotypes; or (d) from plants of different ages from the same cultivar or different cultivars.

In some embodiments, the plant material is harvested from a non-cultivated plant.

In some embodiments, the cultivated plant is a *Cannabis* (marijuana) cultivar or a hemp cultivar.

In some embodiments, the cultivated plant is *Cannabis sativa* subsp. *sativa* var. *sativa, Cannabis sativa* subsp. *sativa* var. *spontanea, Cannabis sativa* subs *P. indica* var. *indica, Cannabis sativa* subs *P. indica* var. *afghanica, Cannabis sativa* subs *P. indica* var. *himalayensis, Cannabis sativa* subsp. *indica* var. *asperrima*, as described in "*A classification of endangered high-THC Cannabis (Cannabis sativa subsp. indica) domesticates and their wild relatives*, John M. McPartland and Ernest Small, PhytoKeys 2020; 144: 81-112. Published online 2020 Apr. 3. doi: 10.3897/phytokeys.144.46700.

Exemplary *Cannabis* cultivars or plant types include but are not limited to, ACDC, Afghan #1, Afgoo, AK-47, Alien OG, Asian Fantasy, Banana Kush, Berry White, Big Sur Holy, Biscotti, Black Jack, Blue Dream, Blueberry, Blueberry Muffin, Bubba Kush, Bubblegum, Candyland, CBG Hemp, Cheese, Chem'91, Chernobyl, Cherry Limeade, Cherry Pie, Cookies, Do-Sa-Do, Durban Poison, Dutch Crunch, G-13, Gas, Gelato, GG #4, GMO Cookies, Golden Pineapple, Guava Jelly CBD, Harlequin, Haze, Headband, Hindu Kush, Ice Cream Cake, Jack Herer, Jilly Bean, Kosher Kush, Kryptonite, LA Confidential, Lemongrass, MAC1, Magic Melon, Malawi Gold, NaPali Pink, New York City Diesel, Northern Lights, Northern Lights #5× Haze, OG Kush, Pincher Creek, Pineapple Upside Down Cake, Purple Punch, Purps, Remedy, Runtz, S.A.G.E., Sensi Star, Skunk #1, Skywalker OG, Sour Diesel, Sour Tangie, Stardawg, Strawberry Banana, Strawberry Cough, Sunset Sherbet, Tahquitz OG, Tangerine Dream, Tangie, The Bling, The White, Trainwreck, Vanilla Frosting, Venom OG, Wedding Cake, White Widow, Zeta, and Zkittlez (See, e.g., Backes, Michael, *Cannabis* Pharmacy: The Practical Guide to Medical Marijuana, Black Dog and Levanthal Publishers, 2017.)

Exemplary hemp cultivars include but are not limited to, Abacus, AC Diesel, ACDC, Acid Rock, Berry Blossom, Berry Exotic, Black Rose, Blue Dream CBD, Blueberry Banana Bread, Boax, Boax Bubblegum, Cannatonic, Cascades, Casino Cookies, Chardonnay, Charlotte's Cherries, Charlotte's Web, Cherry 5, Cherry, Cherry Sweet, Cherry Wine, Frosted Lime, Gewürztraminer CBD, Green Gum, Guava Jam, Harlequin, Healthy Heart, Hawaiian Haze, Hot Blonde, Honolulu Haze, Jupiter, K.O., Lemon Drop, Lifter, Oregon OG, Otto II, Pineberry, Primo Cherry, Purple Boax, Queen Dream, Rainbow Gummeez, Sour J, Sour Space Candy®, Special Sauce®, Spectrum, Stem Cell, Sunset Road Sherbet, Super Lemon Haze CBD, Suver Haze, Sweet CBD, T1 Trump, Watermelon Haze CBD, White CBG®, and the Wife.

In some embodiments, the fresh plant material that is dried and chopped may include an herbal plant or a flowering plant, for example, hops, basil, mimosa, passion flower, corn silk, rose petals, lotus leaf, licorice root, jasmine, ginseng, red clover flowers, bergamot, lemon, lime, sweet orange, tangerine, mandarin, cinnamon bark, citronella, lemongrass, petitgrain, palmarosa, patchouli leaves, geranium, lavender, rosemary, spike lavender, ginger, vetiver, jasmine, neroli (orange blossom), and ylang-ylang.

Harvesting Plants

Plants of one or more plant types may be harvested at any point in their life cycle. The source of the fresh plant material may be a pre-flowering plant, a flowering plant, or a post-flowering plant.

Any parts of a plant may be harvested and included in the plant material. For example, leaves, inflorescences (flowers), trichomes, needles, twigs, fruits, seeds, bark, and roots. In some embodiments, inflorescences (flowers) and trichomes are selectively harvested.

In some embodiments, the plants are *Cannabis* plants and the inflorescences and trichomes comprise from about 5% to 25%, 10% to 35%, 35% to 50%, 50% to 60%, 60% to 70%, 70% to 80%, 80% to 90%, or from about 90% to 100%, for example, at least about 50%, 55%, 60%, 65%, 70%, 75%, 80%, 85%, 90%, 95%, 98%, or at least about 99% of the harvested plant material.

As soon as possible after harvest, the plant material is processed in different ways depending on whether the plant material is to be used as "plant material substrate" or as a source of an EOI extract. For example, plant material to be used as "plant material substrate", is dried, then chopped or granulated as described below to produce granules of dried plant material. Plant material to be used as the source of an EOI extract may be frozen after harvest and processed as described below.

Drying and Chopping/Granulating Fresh Plant Material— Generating a Substrate

The process of making the plant products disclosed herein starts with live plants. A wide variety of approaches to drying plant material is employed by those of skill in the art. Common practices include drying by hanging in the dark in a low temperature, moderate relatively humidity environment, followed by a "curing" step, however, there is no standard for temperature, humidity or time.

In some embodiments, plant material is dried, chilled, or frozen as soon as possible after harvest.

In some embodiments, the drying process for the plant substrate material is started as soon as possible after harvest, for example, within about 10 to 300 minutes, 15 to 280, 20 to 260, 25 to 240, 30 to 220, 35 to 200, 40 to 180, 45 to 160, 50 to 140, 55 to 120, 60 to 100, or within about 65 to 80 minutes after harvest, for example, within 10, 15, 20, 25, 30, 35, 40, 45, 50, 55, 60, 65, 70, 75, 80, 85, 90, 95, 100, 110, 115, 120, 125, 130, 135, 140, 145, 150, 155, 160, 165, 170, 175, 180, 185, 190, 195, 200, 210, 215, 220, 225, 230, 235, 240, 245, 250, 255, 260, 265, 270, 275, 280, 285, 290, 295, or 300 minutes after harvest.

In some embodiments, the harvested plant material to be used as plant substrate is dried at a temperature of from about 45° F. to 65° F., e.g., about 55° F., for a time period of from about 96 to 504 hours, wherein the drying process results in a dried plant product having a moisture content of about 7 to 14% w/w.

Exemplary drying methods include, but are not limited to, conventional drying, vacuum-assisted drying, microwave vacuum-assisted drying, freeze-drying, microwave freeze drying, vacuum-assisted microwave freeze drying, convection heating-assisted vacuum drying, or any combination of the above that yields a dried plant product with a moisture content of 7-14% w/w wherein the temperature is maintained at about 45° F. to 65° F., for example, about 48° F. during the drying process.

In some embodiments, the harvested plant material to be used as plant substrate is dried at a temperature of from about 25° F. to 65° F., 30° F. to 60° F., 35° F. to 55° F., or from about 40° F. to 50° F., for example, 25° F., 26° F., 27° F., 28° F., 29° F., 30° F., 31° F., 32° F., 33° F., 34° F., 35° F., 36° F., 37° F., 38° F., 39° F., 40° F., 41° F., 42° F., 43° F., 44° F., 45° F., 46° F., 47° F., or 48° F., 49° F., 50° F., 51° F., or 52° F., 53° F., 54° F., 55° F., or 56° F., 57° F., 58° F., 59° F., 60° F., 61° F., 62° F., 63° F., 64° F., or 65° F.

The harvested plant material may be dried at a temperature or temperature range until the moisture content is from about 7% to about 14%, for example, for a time period of from about 96 to 504 hours, 120 to 480 hours, 144 to 456 hours, 168 to 432 hours, 192 to 408 hours, 216 to 384 hours, 240 to 360 hours, 264 to 336 hours, or from about 288 to 312 hours to a yield plant material substrate..

In some embodiments, the harvested plant material to be used as a plant substrate has a moisture content of about 7-14% w/w, 8-13% w/w, 9-12% w/w, or about 10-11% w/w, for example, a moisture content of about 7%, 8%, 9%, 10%, 11%, 12%, 13%, or about 14%.

The fraction to be used as plant material substrate is dried then stored frozen until chopped, then chopped just below freezing.

In some embodiments, the dried plant material to be used as plant material substrate is maintained at a temperature below freezing until it is further processed, for example, from about 20° F. to about 0° F., from about 15° F. to about 5° F., from about 10° F. to about 0° F., about −20° F., −19° F., −18° F., −17° F., −16° F., −15° F., −14° F., −13° F., −12° F., −11° F., −10° F., −9° F., −8° F., −7° F., −6° F., −5° F., −4° F., −3° F., −2° F., −1° F., or 0° F. The cold temperature serves to arrest off-gassing of volatile components of the EOI from harvested plant material.

It is known in the art for plant material such as frozen or dried fresh *Cannabis* plant material to be processed by methods including grinding, slicing, shredding, milling, chopping, pulverizing, and sifting through a mesh screen. Often the temperature and humidity are not controlled and valuable EOI components are lost during processing. A number of grinders and milling machines are commercially available and promoted as efficient tools to quickly convert large volumes of *Cannabis* plant material to a precise particle size. These processes typically result in damage to the plant material due to friction, and often generate heat resulting in evaporative loss of volatile compounds and collection of resin on the processing equipment. It follows that such processes can result in a loss of the EOI.

The inventor has discovered that optimal processing of plant material includes a low friction process and may also include temperature control. In the processes described herein, dried plant material may be processed in any manner that minimizes damage to plant morphology and minimizes loss of the EOI by aerosolization and other means. In some exemplary methods designed to preserve plant morphology and minimize loss of the EOI include chopping or granulating at low temperature, e.g., at a temperature of from about 0° F. to 50° F., 5° F. to 45° F., 10° F. to 40° F., 15° F. to 35° F., 20° F. to 35° F., or about 25° F. to 30° F., for example, 0° F., 1° F., 2° F., 3° F., 4° F., 5° F., 6° F., 7° F., 8° F., 9° F., 10° F., 11° F., 12° F., 13° F., 14° F., 15° F., 16° F., 17° F., 18° F., 19° F., 20° F., 21° F., 22° F., 23° F., 24° F., 25° F., 26° F., 27° F., 28° F., 29° F., 30° F., 31° F., 32° F., 33° F., 34° F., 35° F., 36° F., 37° F., 38° F., 39° F., 40° F., 41° F., 42° F., 43° F., 44° F., 45° F., 46° F., 47° F., 48° F. 49° F., or 50° F. In some embodiments, the dried plant material may be processed at room temperature in a manner that minimizes damage to plant morphology and minimizes loss of the EOI by aerosolization and other means.

In some embodiments, dried plant material is chopped. In some embodiments, dried plant material is chopped with a blade (rather than ground, milled, or pulverized as is common in the art). In some embodiments, the plant material is granulated.

In some embodiments, the dried plant material is chopped to yield pieces of dried plant material having a size of about 1-8 mm in diameter, 2-7 mm, 3-6 mm, 4-8 mm or about 5-6 mm in diameter, for example, 1 mm, 2 mm, 3 mm, 4 mm, 5 mm, 6 mm, 7 mm, or about 8 mm in diameter. In some embodiments, chopping is accomplished using chilled blades in a chilled vessel. In some embodiments, chopping is accomplished in a chilled room. In some embodiments, each plant type (also referred to herein as a "cultivar" or "chemotype") is chopped independently.

The chopping or granulating step is carried out in a manner that avoids resin build-up on the chopping equipment. In some embodiments, equipment and containers used for the chopping/granulating step has a non-stick surface, for example, a ceramic coating or fluorine-doping of blades used for chopping.

In some embodiments, the dried and chopped plant material substrate is stored under conditions of about 53-58% RH, for example, about 53% RH, 54% RH, 55% RH, 56% RH, 57% RH, or about 58% RH and a temperature of from about −4 to 55° F., 0° F. to 50° F., 5° F. to 45° F., 10° F. to 40° F., 15° F. to 35° F., or from about 20° F. to 30° F., for example, −4° F., −3° F., −2° F., −1° F., 0° F., 1° F., 2° F., 3° F., 4° F., 5° F., 6° F., 7° F., 8° F., 9° F., 10° F., 11° F., 12° F., 13° F., 14° F., 15° F., 16° F., 17° F., 18° F., 19° F., 20° F., 21° F., 22° F., 23° F., 24° F., 25° F., 26° F., 27° F., 28° F., 29° F., 30° F., 31° F., 32° F., 33° F., 34° F., 35° F., 36° F., 37° F., 38° F., 39° F., 40° F., 41° F., 42° F., 43° F., 44° F., 45° F., 46° F., 47° F., 48° F., 49° F., 50° F., 51° F., 52° F., 53° F., 54° F. or about 55° F.

EOI Extract and Processing—Manufacturing

As soon as possible after harvest, fresh plant material to be used to generate an EOI extract is kept at a temperature ranging from about −90° F. to 48° F., −80° F. to 40° F., −70° F. to 30° F., −60° F. to 20° F., −50° F. to 10° F., −40° F. to 20° F., −30° F. to 30° F., −20° F. to 40° F., or from about −10° F. to 48° F., for example −90° F., −89° F., −88° F., −87° F., −86° F., −85° F., −84° F., −83° F., −82° F., −81° F., −80° F., −79° F., −78° F., −77° F., −76° F., −75° F., −74° F., −73° F., −72° F., −71° F., −70° F., −69° F., −68° F., −67° F., −66° F., −65° F., −64° F., −63° F., −62° F., −61° F., −60° F., −59° F., −58° F., −57° F., −56° F., −55° F., −54° F., −53° F., −52° F., −51° F., −50° F., −49° F., −48° F., −47° F., −46° F., −45° F., −44° F., −43° F., −42° F., −41° F., −40° F., −39° F., −38° F., −37° F., −36° F., −35° F., −34° F., −33° F., −32° F., −31° F., −30° F., −29° F., −28° F., −27° F., −26° F., −25° F., −24° F., −23° F., −22° F., −21° F., −20° F., −19° F., −18° F., −17° F., −16° F., −15° F., −14° F., −13° F., −12° F., −11° F., −10° F., −9° F., −8° F., −7° F., −6° F., −5° F., −4° F., −3° F., −2° F., −1° F., or 0° F., (degrees Fahrenheit).

In one exemplary embodiment, as soon as possible after harvest, fresh plant material is frozen at the harvest site and stored frozen at a temperature described above during transport to the manufacturing site.

A sample of the plant material that is frozen may be examined using any method effective to determine the size of trichome gland heads, for example, scanning electron microscopy ("SEM") or optical microscopy to determine the range of trichome gland head sizes, so that optimal sieve sizes are employed in the separation process.

At the manufacturing site, the fresh plant material to be used to generate an EOI extract is stored at a temperature ranging from about −90° F. to 60° F., −85° F. to 55° F., −80° F. to 50° F., 80° F. to 45° F., −80° F. to 40° F., −70° F. to 30° F., −60° F. to 20° F., −50° F. to 10° F., −40° F. to 20° F., −30° F. to 30° F., −20° F. to 40° F., −20° F. to 45° F., −15° F. to 50° F., −15° F. to 55° F., or from about −10° F. to 60° F., for example −90° F., −89° F., −88° F., −87° F., −86° F., −85° F., −84° F., −83° F., −82° F., −81° F., −80° F., −79° F., −78° F., −77° F., −76° F., −75° F., −74° F., −73° F., −72° F., −71° F., −70° F., −69° F., −68° F., −67° F., −66° F., −65° F., −64° F., −63° F., −62° F., −61° F., −60° F., −59° F., −58° F., −57° F., −56° F., −55° F., −54° F., −53° F., −52° F., −51° F., −50° F., −49° F., −48° F., −47° F., −46° F., −45° F., −44° F., −43° F., −42° F., −41° F., −40° F., −39° F., −38° F., −37° F., −36° F., −35° F., −34° F., −33° F., −32° F., −31° F., −30° F., −29° F., −28° F., −27° F., −26° F., −25° F., −24° F., −23° F., −22° F., −21° F., −20° F., −19° F., −18° F., −17° F., −16° F., −15° F., −14° F., −13° F., −12° F., −11° F., −10° F., −9° F., −8° F., −7° F., −6° F., −5° F., −4° F., −3° F., −2° F., −1° F., 0° F., 1° F., 2° F., 3° F., 4° F., 5° F., 6° F., 7° F., 8° F., 9° F., 10° F., 11° F., 12° F., 13° F., 14° F., 15° F., 16° F., 17° F., 18° F., 19° F., 20° F., 21° F., 22° F., 23° F., 24° F., 25° F., 26° F., 27° F., 28° F., 29° F., 30° F., 31° F., 32° F., 33° F., 34° F., 35° F., 36° F., 37° F., 38° F., 39° F., 40° F., 41° F., 42° F., 43° F., 44° F., 45° F., 46° F., 47° F., 48° F., 49° F., 50° F., 51° F., 52° F., 53° F., 54° F., 55° F., 56° F., 57° F., 58° F., 59° F., or 60° F. (degrees Fahrenheit).

In some embodiments of the process for making an extract of an EOI resin, procedures routinely employed by those of skill in the art are employed. See, for example, https://www.alchimiaweb.com/blogen/make-ice-water-hash/. It is believed that the cold water results in separation of trichome gland heads (containing EOI) from trichome stalks. Successive sieve or screen with pore sizes ranging from about 40-240μ may be used to concentrate the EOI extract, resulting in a highly purified extract/EOI fraction captured through mechanical means.

The process disclosed herein may include the steps of placing chilled or frozen plant material in a cold slurry of distilled water and distilled water ice, and agitating, for example for about 5 to 15 minutes. Following agitation, the plant material cold water slurry may be allowed to rest, then it is passed through a series of sieves or screens having pore sizes of from about 40-240μ. Initially the trichome gland heads pass through a sieve/screen with a pore size of from about 220-240μ. Sieves/screens are used in descending order of pore size with the 120μ and smaller pore size screens yielding an EOI resin extract. The process may be repeated to obtain the maximum amount of EOI resin extract.

In an alternate embodiment, the chilled or frozen plant material is processed by solvent extraction to generate an EOI resin extract. In some embodiments, pressurized solvent gases such as butane, heptane, propane, pentane, refrigerant gases, or liquid CO2 at cold temperatures, e.g., −76° F. to −220° F. are used. Numerous procedures for cold temperature solvent extraction of plant material, e.g., *Cannabis* are known and routinely employed by those of skill in the art.

The process disclosed herein includes the additional step of processing the extracted EOI resin to generate THCa crystals and a high terpene extract (HTE).

In some embodiments this is accomplished by carrying out the step of expelling (mechanically pressing) the EOI resin through a sieve or screen under pressure to a temperature of from about 45° F. to about 150° F., 45° F. to about 140° F., 45° F. to about 130° F., 45° F. to about 120° F., 45° F. to about 110° F., 45° F. to about 100° F., 45° F. to about 85° F., 55° F. to 100° F., 65° F. to 110° F., 75° F. to 120° F., 85° F. to 130° F., 95° F. to 140° F., or from about 100° F. to 150° F., for example, 45° F., 46° F., 47° F., 48° F., 49° F., 50° F., 51° F., 52° F., 53° F., 54° F., 55° F., 56° F., 57° F., 58° F., 59° F., 60° F., 61° F., 62° F., 63° F., 64° F., 65° F., 66° F., 67° F., 68° F., 69° F., 70° F., 71° F., 72° F., 73° F., 74° F., 75° F., 76° F., 77° F., 78° F., 79° F., 80° F., 81° F., 82° F., 83° F., 84° F., 85° F., 90° F., 95° F., 100° F., 105° F., 110° F., 115° F., 120° F., 125° F., 130° F., 135° F., 140° F., 145° F., or about 150° F. See, for example, https://www.alchimiaweb.com/blogen/make-thca-crystals-solventless-sauce/.

In some embodiments, the expelling process includes use of a sieve, screen or mesh bag having a pore size of from about 10 to 40 microns, 15 to 35 or about 20 to 30 microns, for example, about 10, 11, 12, 13, 14, 15, 16, 17, 18, 19, 20, 21, 22, 23, 24, or about 25 microns.

In some embodiments expelling is carried out using a mesh bag with a pore size of 15 to 45 microns, 20 to 35 or about 25 to 30 microns, for example, about 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, or about 45 microns.

In some embodiments, the expelling process includes use of a sieve, screen or mesh bag at a pressure of from 100 to 500 psi, 125 to 475, 150 to 450, 175 to 375, 200 to 350, 225 to 325, or about 250 to 300 psi.

In some embodiments, the expelling process includes use of a sieve, screen or mesh bag under mechanical pressure at a temperature of from about 45° F. to about 200° F., 45° F. to about 190° F., 45° F. to about 180° F., 45° F. to about 170° F., 45° F. to about 160° F., 45° F. to about 150° F., 50° F. to about 180° F., 50° F. to about 160° F., 50° F. to about 140° F., 50° F. to about 120° F., 50° F. to about 100° F., 60° F. to about 200° F., 65° F. to about 190° F., 70° F. to about 185° F., 75° F. to about 180° F., 80° F. to about 175° F., 85° F. to about 170° F., 90° F. to about 165° F., 95° F. to about 160° F., 100° F. to about 155° F., 105° F. to about 150° F., 110° F. to about 145° F., 115° F. to about 135° F., or from about 120° F. to about 200°.

In some embodiments, the expelling process includes incubating the EOI resin extract at a temperature of from about 40° F. to about 100° F., 45° F. to 95° F., 50° F. to 90° F., 55° F. to 85° F., 60° F. to 80° F., 60° F. to 75° F., 60° F. to 70° F., or from about 60° F. to 65°, for a time sufficient for the THCa to crystalize.

In some embodiments, the process includes incubating the EOI resin extract for 7 days to 30 days at 0° C. to 15° C. (30° F. to 60° F.) to allow THCa to crystalize. In some embodiments, the THCa crystallizes in less than 7 days.

In some embodiments, the process includes seeding the EOI resin extract with crystals of THCa for a time sufficient for THCa to crystalize, e.g., for 1 day, 2 days, 3 days, 4 days, 5 days, 6 days, or 7 days to 30 days at 0° C. to 15° C. (30° F. to 60° F.).

The process may include seeding the EOI resin extract with crystals of THCa for 7 days to 30 days, e.g., 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days, at 30° F. to 60° F., e.g., 30° F., 31° F., 32° F., 33° F., 34° F., 35° F., 36° F., 37° F., 38° F., 39° F., 40° F., 41° F., 42° F., 43° F., 44° F., 45° F., 46° F., 47° F., 48° F., 49° F., 50° F., 51° F., 52° F., 53° F., 54° F., 55° F., 56° F., 57° F., 58° F., 59° F., or 60° F. to allow THCa to crystalize out.

In some embodiments, following incubation for 3 days to 30 days at 0° to 15° C. (30° F. to 60° F.), the THCa is separated out by centrifugation and removed resulting in a THCa-reduced EOI extract.

In some embodiments, the THCa crystallization process is repeated one or more times.

In some embodiments, before or after the THCa is reduced or removed, the EOI extract is stored at a temperature of from about –184° F. to 50° F., –184° F. to 45° F., –184° F. to 40° F., –184° F. to 35° F., –184° F. to 30° F., –184° F. to 25° F., –170° F. to 50° F., –160° F. to 50° F., –150° F. to 50° F., –140° F. to 50° F., –130° F. to 50° F., –120° F. to 50° F., –120° F. to 40° F., –110° F. to 40° F., –100° F. to 40° F., or from about –100° F. to 40° F., for example –184° F., –180° F., –170° F., –160° F., –150° F., –140° F., –130° F., –120° F., –110° F., –100° F., –90° F., –80° F., –70° F., –60° F., –50° F., –40° F., –30° F., –20° F., –10° F., –4° F., 0° F., 10° F., 15° F., 20° F., 25° F., 30° F., 35° F., 40° F., 45° F., or 50° F. (degrees Fahrenheit).

Processes routinely employed by those of skill in the art include a step where THCa crystals (the THC fraction) and an EOI extract are recombined. Contrary to such routine processes, in the disclosed processes, in some embodiments the THCa crystals are not used to make the final plant product. A novel and nonobvious feature of the processes disclosed herein is that the THCa crystals may not be included in the final step of the claimed process and may not be a component of the final plant product. In some embodiments, the THCa crystals are discarded. In some embodiments, the THCa crystals are used for another purpose.

In some embodiments, "powdered or liquid cannabinoids are added to the *Cannabis* plant product obtain a desired and consistent level of THCa or THC, or as needed to meet the defined chemistry of a given formulation.

Formulations

A customized and desired EOI is created using the analytics from one or more of, (a) pre-harvest plant material, (b) post-harvest EOI extract, (c) post-harvest dried plant substrate material, and (d) post-harvest dried and chopped plant substrate material. In some embodiments, the results of the analysis of (a)-(d) above is used to design a formulation to create the desired EOI in the finished plant product. In some embodiments, tools such as databases, crop chemistry, statistics, analytics, computational chemistry and computational pharmacology software, and artificial intelligence (AI) systems are used to guide design of the formulation.

In some embodiments, the EOI is customized at the request of a customer, for example a combination of fragrant and flavorful compounds including one or more terpenes (monoterpenes, diterpenes, sesquiterpenes, terpenoids, and terpene alcohols), esters, ethers, thiols, and aldehydes is added to *Cannabis* flower. In some embodiments, this is accomplished while the customer waits.

After characterization and analysis/quantification of EOI (s) from the materials described above, they are combined to form a novel EOI not produced by any single cultivar. This process allows for transfer of an EOI between or among different plant types, e.g., cultivars or chemotypes, by the addition and mixing of one or more EOIs to a different substrate or to a mixture of substrates. For example, the EOI of a mature plant may be added to the substrate of an immature plant of the same plant type or a different plant type.

Non-limiting examples of customized *Cannabis*-based plant products include a product where, (a) the EOI is derived from the combination of a low THC substrate from an immature plant, e.g., hemp, with a high terpene content EOI from a mature plant, (b) a high-ocimene EOI, e.g., from a Skunk *Cannabis* cultivar mixed with a high-limonene, caryophyllene, myrcene substrate from a Kush *Cannabis* cultivar. The ability to customize *Cannabis*-based plant products using natural ingredients is a novel and nonobvious feature of the plant products and processes disclosed herein. In order to customize the EOI, the EOI in the components to be mixed are analyzed and quantified to enable the design of each formulation, e.g., the best blending ratio of the EOI into the substrate, to produce a plant product with a reliable and consistent EOI.

In some embodiments, after processing plant material from the one or more *Cannabis* or hemp plant types to generate an EOI extract, the post-extraction biomass which lacks or substantially lacks an EOI (the desired and recoverable portion of all plant compounds that impact the physiological, psychological, or drug effect, hedonic effect, and/or fragrance and flavor effect) is dried and processed, then reinfused with an EOI which includes cannabinoids.

In one embodiment, the spent biomass may be infused with cannabinoids and terpenoids to restore to freshly harvested levels.

In one embodiment, the spent biomass may be converted to hemp paper then infused with a desired terpenoid/cannabinoid EOI.

In one embodiment, old or damaged *Cannabis* is "rejuvenated" by infusion with a selected EOI.

Mixing to Make the Plant Product

The process of making the plant product further includes adding an EOI extract alone or in combination with additional terpenes to a substrate, prepared as described above. In some embodiments, the EOI extract alone is added to the substrate with mixing until the EOI extract has been uniformly absorbed onto the substrate resulting in a plant product comprising a desired EOI. In some embodiments, additional terpenes (monoterpenes, diterpenes, sesquiterpenes, terpenoids, and terpene alcohols), esters, ethers, thiols and aldehydes are added to the mixture to obtain the desired EOI. In some embodiments, a cannabinoid, e.g., THCa, Δ9-THC, Δ8-THC, THCV, CBDa, CBD, CBDV, CBN, CBGa, CBG, or CBC in acidic and neutral, and propyl and pentyl forms is added to the EOI extract or mixture to obtain the desired EOI.

All of the process steps are carried out under conditions of temperature and humidity as described herein to provide for maximum preservation of the EOI.

In some embodiments, the mixing step is carried out at a temperature of from about 0° F. to 65° F., from about 5° F. to 60° F., from about 5° F. to 55° F., from about 5° F. to 50° F., from about 5° F. to 45° F., from about 10° F. to 60° F., from about 10° F. to 55° F., from about 10° F. to 50° F., from about 10° F. to 45° F., from about 15° F. to 60° F., from about 15° F. to 55° F., from about 15° F. to 50° F., from about 15° F. to 45° F., for example, about 0° F., 1° F., 2° F., 3° F., 4° F., 5° F., 6° F., 27° F., 8° F., 9° F., 10° F., 11° F., 12° F., 13° F., 14° F., 15° F., 16° F., 17° F., 18° F., 19° F., 20° F., 21° F., 22° F., 23° F., 24° F., 25° F., 26° F., 27° F., 28° F., 29° F., 30°
F., 31° F., 32° F., 33° F., 34° F., 35° F., 36° F., 37° F., 38° F.,
39° F., 40° F., 41° F., 42° F., 43° F., 44° F., 45° F., 46° F., 47°
F., 48° F., 49° F., 50° F., 51° F., 52° F., 53° F., 54° F., 55° F.,
56° F., 57° F., 58° F., 59° F., 60° F., 61° F., 62° F., 63° F., 64°
F., or about 65° F.

In some embodiments, the mixing step is carried out at a
relative humidity of from about 50 to 60% RH, for example,
50%, 51%, 52%, 53%, 54%, 55%, 56%, 57%, 58%, 59%, or
a RH of about 60%.

In some embodiments, a nonstick container such as a
platinum silicone or ceramic-coated steel bowl is used for
the mixing process.

In some embodiments, a mechanical electric planetary
mixer with a silicone mixing paddle or whisk is used to
slowly and thoroughly mix the substrate and EOI extract.
Techniques akin to those known in the tobacco processing
arts such as topdressing and casing may be employed during
the mixing process.

Incorporation of the EOI extract into the substrate may be
mostly complete when no oil or clumping is visible in the
mixture or on the surface of the mixing container or imple-
ment. At this point, the mixture may be placed in a mold and
gently pressed one or more times, then fluffed and packed.

In some embodiments, a blend of substrates from different
plant types are mixed with an EOI extract from one plant
type to make a finished plant product with a desired EOI
formulation.

In some embodiments, a blend of substrates from different
plant types are mixed with a blend of EOI extracts from
different plant types to make a finished plant product with a
desired EOI formulation.

In some embodiments, a substrate from one plant type is
mixed blend of EOI extracts from different plant types to
make a finished plant product with a desired EOI formula-
tion.

In some embodiments, the process steps are conducted in
a manufacturing facility.

While not wishing to be bound by theory, once the EOI
extract has bound to the plant substrate, a degree of stabi-
lization within the mixture is achieved that may slow
off-gassing of monoterpenes.

Finishing and Storing the Plant Product

In some embodiments, the finished plant product is mixed
with 0.2 to 5.0%, 0.2 to 4.5%, 0.2 to 4.0%, 0.2 to 3.5%, 0.2
to 3.0%, 0.2 to 2.5%, 0.2 to 2.0%, 0.5% or more, 0.6% or
more, 0.7% or more, 0.8% or more, 0.9% or more, 1.0% or
more, 1.1% or more, 1.2% or more, 1.3% or more, 2.1% or
more, 2.2% or more, 2.3% or more, 2.4% or more, 2.5% or
more, 2.6% or more, 2.7% or more, 2.8% or more, 2.9% or
more, 3.0% or more, 3.1% or more, 3.2% or more, 3.3% or
more, 3.4% or more, 3.5% or more, 3.6% or more, 3.7% or
more, 3.8% or more, 3.9% or more, or 4.0% or more micro
pulverized *Cannabis* leaf.

In some embodiments, the finished plant product is
treated with a sealer coating comprising a plant cellulose
compound to reduce migration of the EOI and lipids from
the plant mixture to the cigarette paper.

In some embodiments, the finished plant product is pro-
vided to consumers in the form of pellets, in a loosely
packed form, in a joint or cigarette, or as part of a kit.

In some embodiments, the finished plant product is used
to make cigarettes, e.g., pre-rolls. The cigarettes may include
the novel and nonobvious feature of having a crutch, filter,
or tip at each end of the cigarette, referred to herein as a
"Perfecto".

The crutch, filter or tip provides the advantages of pre-
venting the plant product from falling out of the rolled
cigarette, and more importantly allows the cigarette to be cut
or divided into two arbitrary sized portions.

In some embodiments, the finished plant product is pro-
vided as a small pre-roll, referred to herein as a "Quickie".

In some embodiments, an additional component may be
added to the plant product in a variety of ways prior to or
during the process of making the cigarette. e.g., applied to
plant product by spraying, encapsulated by spraying or
dusting, or within the casing, crutch, filter or tip.

In some embodiments, the headspace of the holding
hopper of an automated cigarette rolling machine (contain-
ing the infused biomass) is saturated with aerosolized EOI to
minimize off-gassing of volatile fragrant and flavorful com-
pounds from the infused biomass, some of which may
modulate or modify the effects of cannabinoids.

In some embodiments, a system and method for creating
pre-rolls that fills and packs pre-rolled papers with plant
product efficiently and with consistent results is provided.

In some embodiments, the plant product is stored at a
temperature of from about −86° F. to about 60° F., from
about −86° F. to 55° F., from about −86° F. to 50° F., from
about −86° F. to 45° F., from about −80° F. to 60° F., from
about −80° F. to 50° F., from about −80° F. to 40° F., from
about −70° F. to 60° F., or from about −70° F. to 50° F., from
about −20° F. to 60° F., from about −20° F. to 55° F., from
about −20° F. to 50° F., from about −20° F. to 45° F., e.g.,
about: −86° F., −85° F., −84° F., −83° F., −82° F., −81° F.,
−80° F., −79° F., −78° F., −77° F., −76° F., −75° F., −74° F.,
−73° F., −72° F., −71° F., −70° F., −69° F., −68° F., −67° F.,
−66° F., −65° F., −64° F., −63° F., −62° F., −61° F., −60° F.,
−59° F., −58° F., −57° F., −56° F., −55° F., −54° F., −53° F.,
−52° F., −51° F., −50° F., −49° F., −48° F., −47° F., −46° F.,
−45° F., −44° F., −43° F., −42° F., −41° F., −40° F., −39° F.,
−38° F., −37° F., −36° F., −35° F., −34° F., −33° F., −32° F.,
−31° F., −30° F., −29° F., −28° F., −27° F., −26° F., −25° F.,
−24° F., −23° F., −22° F., −21° F., −20° F., −19° F., −18° F.,
−17° F., −16° F., −15° F., −14° F., −13° F., −12° F., −11° F.,
−10° F., −9° F., −8° F., −7° F., −6° F., −5° F., −4° F., −3° F.,
−2° F., −1° F., 0° F., 1° F., 2° F., 3° F., 4° F., 5° F., or 6° F.,
7° F., 8° F., 9° F., 10° F., 11° F., 12° F., 13° F., 14° F., 15°
F., 16° F., 17° F., 18° F., 19° F., 20° F., 21° F., 22° F., 23° F.,
24° F., 25° F., 26° F., 27° F., 28° F., 29° F., 30° F., 31° F., 32°
F., 33° F., 34° F., 35° F., 36° F., 37° F., 38° F., 39° F., 40° F.,
41° F., 42° F., 43° F., 44° F., 45° F., 46° F., 47° F., 48° F., 49°
F., 50° F., 51° F., 52° F., 53° F., 54° F., 55° F., 56° F., 57° F.,
58° F., 59° F., or about 60° F. for maintenance of the EOI.
The plant product may be stored for at least 1 week, 2 weeks,
3 weeks, 1 month, 2 months, 3 months, 4 months, 5 months,
6 months, 7 months, 8 months, 9 months, 10 months, 11
months, 12 months, 18 months, 24 months, 36 months, 48
months, 60 months, 30 days, 40 days, 50 days, 60 days, 70
days, 80 days, 90 days or more. Colder temperatures are
preferred for long term storage and preservation of the EOI.

In one embodiment, at least 95%, at least 90%, at least
85%, at least 80%, at least 75%, at least 70%, at least 65%,
at least 60%, at least 55%, or at least 50%, of the total
terpene content in the plant product is stably maintained for
at least 30 days, 40 days, 50 days, 60 days, 70 days, 80 days,
90 days or up to 11 months or more when stored, (a) at a
temperature of from about −90° F. to 48° F., from about −86°
F. to about 40° F., from about −70° F. to 35° F., from about
−51° F. to 35° F., from about −20° F. to 35° F., from about
−10° F. to 40° F. or from about −5° F. to 35° F., e.g., about
−86° F., about −51° F., about 0° F., about 24° F., about 34°
F., or about 40° F., (b) under vacuum, (c) in the presence of
oxygen absorption materials, (d) in modified atmosphere
packaging, and/or (e) at room temperature.

In one embodiment, at least 95%, at least 90%, at least
85%, at least 80%, at least 75%, at least 70%, at least 65%,
at least 60%, at least 55%, or at least 50%, of the amount of
one or more monoterpenes in the plant product is stably
maintained for at least 30 days, 40 days, 50 days, 60 days, 70 days, 80 days, 90 days or up to 11 months or more when stored, (a) at a temperature of from about −90° F. to 48° F., from about −86° F. to about 40° F., from about −70° F. to 35° F., from about −51° F. to 35° F., from about −20° F. to 35° F., from about −10° F. to 40° F. or from about −5° F. to 35° F., e.g., about −86° F., about −51° F., about 0° F., about 24° F., about 34° F., or about 40° F., (b) under vacuum, (c) in the presence of oxygen absorption materials, (d) in modified atmosphere packaging, and/or (e) at room temperature.

In one embodiment, at least 95%, at least 90%, at least 85%, at least 80%, at least 75%, at least 70%, at least 65%, at least 60%, at least 55%, or at least 50%, of the amount of one or more sesquiterpenes in the plant product is stably maintained for at least 30 days, 40 days, 50 days, 60 about −86° F., about −51° F., about 0° F., about 24° F., about 34° F., or about 40° F., (b) under vacuum, (c) in the presence of oxygen absorption materials, (d) in modified atmosphere packaging, and/or (e) at room temperature.

In one embodiment, at least 95%, at least 90%, at least 85%, at least 80%, at least 75%, at least 70%, at least 65%, at least 60%, at least 55%, or at least 50%, of the amount of one or more terpenoids, terpene alcohols, esters, ethers, thiols and aldehydes are stably maintained for at least 30 days, 40 days, 50 days, 60 days, 70 days, 80 days, 90 days or up to 11 months or more when stored, (a) at a temperature of from about −90° F. to 48° F., from about −86° F. to about 40° F., from about −70° F. to 35° F., from about −51° F. to 35° F., from about −20° F. to 35° F., from about −10° F. to 40° F. or from about −5° F. to 35° F., e.g., about −86° F., about −51° F., about 0° F., about 24° F., about 34° F., or about 40° F., (b) under vacuum, (c) in the presence of oxygen absorption materials, (d) in modified atmosphere packaging, and/or (e) at room temperature.

In one embodiment, the plant product is stored under conditions effective to preserve the EOI in the infused flower material. Such conditions include one or more of storage at: room temperature, a low temperature, storage under vacuum, in the presence of oxygen absorption materials, and/or in modified atmosphere packaging.

Use of the Plant Product

A consumer may use the plant product disclosed herein for smoking, vaporization, infusion, or any other use.

In some embodiments, the plant product disclosed herein is be inhaled through aerosolization using a vaporizer, a pipe, nebulizer, or a vape pen.

In some embodiments, the inhalable *Cannabis* product is a smokable product in the form of a cigarette, a joint, or a "pre-roll".

In some embodiments, the pre-roll comprises a crutch, paper or plant-based tube.

In some embodiments, the pre-roll comprises a crutch, filter or tip at each end.

In some embodiments, the pre-roll is a Perfecto.

In some embodiments, the pre-roll is a Quickie.

In some embodiments, the inhalable *Cannabis* product is provided in a kit, which may include the *Cannabis* product and pipe, vaporizer, papers, or other means to roll the plant product into a joint or cigarette.

EXAMPLES

The disclosure is further illustrated by the following examples. The examples are provided for illustrative purposes only. They are not to be construed as limiting the scope or content of the disclosure in any way.

Example 1. Process for Making Exemplary Plant Products

A. Freshly harvested *Cannabis* plant material of the OG Kush cultivar containing flowers and trichomes was analyzed for cannabinoid and terpene content and divided into 2 fractions. One fraction was placed in a conventional drying room within about 120 minutes following harvest and dried to a moisture content of 11% w/w at a temperature of 55° F. for 168 hours. A sample was retained for analysis and the dried plant material was stored in a container at a temperature of about 48° F. with a relative humidity of about 55% until used.

Some of the dried plant material was removed from storage and chopped slowly using a small scale hand chopper described at https://lift-innovations.com/, to yield a substrate containing pieces of plant material of with an average diameter of 5 mm. Immediately after chopping, the chopped substrate was placed in an insulated stainless steel bowl at a temperature of about 48 F, with a sample retained for analysis.

The second fraction of plant material was frozen at a temperature of −4° F. within 30 minutes following harvest and transported to a manufacturing site. A small sample of plant material was retained for examination by light microscopy to determine the size of trichome gland heads in order to select the proper pore size for the following sieve filtration step.

At a manufacturing site, the frozen plant material was placed in a cold slurry of distilled water and distilled water ice and agitated. After about 5 to 20 minutes of agitation, the mixture was allowed to rest and the slurry was passed through a sieve (with a pore size of about 240 microns) such that the gland heads and resin passed through the sieve along with the water, while the plant material remained in the sieve. The plant material was discarded and the liquid mixture passed through a series of sieves to yield an EOI resin. The EOI resin was collected with sieves having a pore size of 20-220 microns. A sample was retained for analysis.

The EOI resin was aged to allow THCa crystals to nucleate and grow within the whipped resin.

As the aged mixture cooled, THCa crystals formed in the mixture and were easily sieved from the EOI extract, which was collected in a non-stick container and immediately chilled to a temperature of about 48° F., with a sample retained for analysis. Contrary to standard methods known in the art, the THCa crystals were not used to make the plant product and were discarded.

The bowl containing the chopped substrate was then placed within a mechanical electric mixer assembly at a temperature of 48° F. and stirred in a 60 RPM planetary motion with a silicone whisk attached to the mixer. The THCa-reduced EOI extract was slowly drizzled onto the substrate with mixing until the substrate and THCa-reduced EOI extract were thoroughly mixed and no oil or clumping was visible in the mixture, on the surface of the bowl or on the whisk. A small amount of dry substrate was used to wick up remaining THCa-reduced EOI extract and further mixed. The mixture was then removed from the bowl and placed in a mold and gently pressed. This compressed mixture was allowed to rest for about an hour then fluffed with a whisk, compressed again, then the final plant product was fluffed and packed, at a temperature of about 48° F. and a relative humidity of about 55%.

B. In a second study, freshly harvested *Cannabis* plant material of the Jack Herer cultivar was carried through a process substantially the same as described above for Example 1A. The final plant product was stored at a temperature of about 48° F. and a relative humidity of about 55% until use. A sample was analyzed for cannabinoid and terpene content, the results of which are shown in Table 3.

TABLE 3

Results of Cannabinoid and Terpene Analysis of Exemplary Cannabis Samples.

| | OG KUSH flower | Jack Herer flower | Flower (substrate) Jack Herer | EOI 1 terpinolene-dominant extract | EOI 2 Limonene-dominant extract | Perfect Infused Flower Example (200831N016) |
|---|---|---|---|---|---|---|
| Total Terpenes (mg/g) | 14.35 | 3.19 | 13.31 | 245.53 | 226.79 | 55.89 |
| Total Terpenes (%) | 1.44 | 0.32 | 1.33 | 24.55 | 22.68 | 5.59 |
| Terpenes (%) | | | | | | |
| α-Pinene | 0.05 | | 0.02 | 0.34 | 0.38 | 0.08 |
| b-Pinene | 0.06 | | 0.03 | 0.37 | 0.52 | 0.09 |
| b-Myrcene | 0.35 | | 0.09 | 3.83 | 10.90 | 1.22 |
| α-Phellandrene | | | | | 0.25 | |
| Limonene | 0.31 | | 0.13 | 3.25 | 7.10 | 1.16 |
| b-Ocimene | | | 0.08 | 0.51 | 0.53 | 0.09 |
| Terpinolene | | | 0.30 | 4.62 | 0.06 | 0.85 |
| Linalool | 0.14 | 0.03 | 0.04 | 0.14 | 0.13 | 0.13 |
| Fenchol | | | | 0.40 | 0.29 | 0.12 |
| (-)-Isopulegol | | | | | | |
| α-Terpineol | | | 0.03 | 0.14 | 0.15 | 0.09 |
| b-Caryophyllene | 0.41 | 0.19 | 0.39 | 8.77 | 1.28 | 1.32 |
| α-Humulene | 0.12 | 0.06 | 0.15 | 1.41 | 0.32 | 0.22 |
| Valencene | | | 0.01 | 0.03 | 0.02 | 0.01 |
| Nerolidol | | | 0.02 | | | 0.04 |
| Caryophyllene Oxide | | | 0.02 | 0.09 | 0.08 | |
| Guaiol | | | | 0.36 | 0.33 | 0.09 |
| α-Bisabolol | | 0.04 | 0.03 | 0.20 | 0.21 | 0.08 |
| Camphene | | | | 0.07 | 0.09 | |
| Bormeol | | | | 0.04 | 0.04 | |

The final plant material obtained from the studies in Examples 1A and 1B were used to make cigarettes. The cigarettes were constructed in a novel manner such that a crutch was included at each end of the cigarettes, resulting in a product referred to herein as a "Perfecto". The Perfecto can be divided into two arbitrarily sized portions so the consumer can determine how much of the product to smoke at a given time.

C. In further studies, fresh frozen plant material was gathered as described above in Example 1A. The frozen plant material was then cooled to –50° F., and then extracted with butane at high pressure and at –120° F. The resulting EOI resin extract was collected and allowed to rest at 60° F. A small amount of crystalline THCa was added to the EOI resin extract to encourage crystallization of the THCa. After 3 to 30 days, depending on the Cannabis cultivar extracted, a centrifuge was used to separate the THCa crystals from the remaining high terpene extract (HTE). This HTE was sampled and quantitatively analyzed for terpene content on a UHPLC-PDA instrument to confirm entourage content. This process was repeated with different cultivars presenting different chemotypes of interest. Once completed, the HTE extracts are blended together at 55° F. to create an EOI that can be applied to dried chopped plant substrate to yield a variety of different plant products.

Example 2. Product Comparison

Terpene analysis was conducted to compare 4 popular brands of commercially available prerolls (Lift Ticket #1, Lift Ticket #2, Titan OG, and a $75.50 live resin infused preroll), with a sample of Perfect infused flower produced consistent with the disclosure herein. The analysis was conducted a commercial laboratory (SC Labs, Santa Cruz, Calif.). The results are shown in Table 4.

TABLE 4

Results of Terpene Analysis of Exemplary Cannabis Products.

| | Lift Ticket #1 | Lift Ticket #2 | Titan OG | $75.50 live resin infused preroll | Perfect infused flower (200430Q009) |
|---|---|---|---|---|---|
| Total THC (%) | ND | ND | ND | ND | 27.950 |
| Total CBD (%) | ND | ND | ND | ND | 0.080 |
| Total Cannabinoids (%) | ND | ND | ND | ND | 30.210 |
| Total Terpenes (mg/g) | 3.824 | 6.863 | 3.732 | 10.663 | 34.250 |
| Total Terpenes (%) | 0.382 | 0.686 | 0.373 | 1.070 | 3.430 |
| Terpenes (%) | | | | | |
| α-Pinene | 0.010 | 0.004 | 0.006 | | 0.030 |
| b-Pinene | 0.013 | 0.005 | 0.004 | 0.016 | 0.050 |
| b-Myrcene | 0.013 | 0.009 | 0.010 | 0.010 | 0.630 |
| α-Phellandrine | | | | | 0.020 |
| Limonene | 0.044 | 0.024 | 0.027 | 0.066 | 0.695 |
| b-Ocimene | | | | | 0.060 |
| Terpinolene | 0.004 | | 0.004 | | 0.180 |

TABLE 4-continued

Results of Terpene Analysis of Exemplary Cannabis Products.

| | Lift Ticket #1 | Lift Ticket #2 | Titan OG | $75.50 live resin infused preroll | Perfect infused flower (200430Q009) |
|---|---|---|---|---|---|
| Linalool | 0.131 | 0.074 | 0.108 | 0.182 | 0.860 |
| Fenchol | | | | 0.077 | 0.050 |
| (−)-Isopulegol | | | | | |
| α-Terpineol | | | | 0.101 | 0.060 |
| b-Caryophyllene | 0.096 | 0.377 | 0.137 | 0.383 | 0.412 |
| α-Humulene | 0.034 | 0.121 | 0.042 | 0.112 | 0.129 |
| Valencene | | | | 0.006 | 0.010 |
| Nerolidol | | | | | 0.030 |
| Caryophyllene Oxide | | | | 0.040 | 0.030 |
| Guaiol | | | | | 0.070 |
| α-Bisabolol | 0.028 | 0.074 | 0.026 | 0.073 | 0.100 |
| Camphene | 0.005 | | 0.003 | | |
| Geraniol | 0.005 | | 0.006 | | |

These results illustrate the superior terpene content of plant products produced consistent with the disclosure herein.

Example 3. Stability Testing

A sample of infused *Cannabis* flower produced consistent with the disclosure herein was analyzed soon after production, after storage at about 0° F. for 30 days and after storage at about 34° F. for 70 days. The samples were sent to a commercial laboratory (SC Labs, Santa Cruz, Calif.), for analysis. The results are shown in Table 5.

TABLE 5

Stability of Terpenes in Exemplary Cannabis Samples.

| | Stability baseline 200114V006 | 30d stability freezer 200221W004 | 70d stability refrigerator 200221W003 | % of baseline (30d) | % of baseline (70d) |
|---|---|---|---|---|---|
| Total Terpenes (mg/g) | 28.211 | 23.460 | 22.730 | | |
| Total Terpenes (%) | 2.821 | 2.346 | 2.273 | | |
| Terpenes (%) | | | | | |
| α-Pinene | 0.273 | 0.237 | 0.193 | 86.81 | 81.43 |
| b-Pinene | 0.187 | 0.171 | 0.143 | 91.44 | 76.47 |
| b-Myrcene | 0.340 | 0.289 | 0.243 | 85.00 | 71.47 |
| Limonene | 0.341 | 0.319 | 0.271 | 93.55 | 79.47 |
| b-Ocimene | 0.063 | 0.058 | 0.050 | 92.06 | 79.37 |
| Terpinolene | 0.276 | 0.222 | 0.221 | 80.43 | 80.07 |
| Linalool | 0.301 | 0.195 | 0.221 | 64.78 | 73.42 |
| Fenchol | 0.049 | 0.048 | 0.045 | 97.96 | 91.84 |
| α-Terpineol | 0.056 | 0.053 | 0.055 | 94.64 | 98.21 |
| Cedrene | | 0.006 | | | |
| b-Caryophyllene | 0.592 | 0.501 | 0.512 | 84.63 | 86.49 |
| α-Humulene | 0.220 | 0.146 | 0.164 | 66.36 | 74.55 |
| Valencene | 0.058 | | | 0.00 | 0.00 |
| Caryophyllene Oxide | 0.032 | 0.028 | 0.037 | 87.50 | 115.63 |
| Guaiol | 0.029 | 0.027 | 0.030 | 93.10 | 103.45 |
| α-Bisabolol | 0.057 | 0.048 | 0.056 | 84.21 | 98.25 |
| Fenchone | | | 0.031 | | |

The total terpene content and the percentages of individual terpenes of an exemplary *Cannabis* plant product ("Night Cap" formulation) were substantially unchanged for approximately 11 months when stored at room temperature. On 1/18/2022 the total terpene content was 25.93 mg/g (2.59%) and on 12/9/2022 was 24.24 mg/g, (2.42%) as shown in Table 6. This data demonstrates the stability of the disclosed *Cannabis* plant product for approximately 11 months at room temperature. The table also shows the wide variety of flavors and fragrances that are attributed to different terpenes.

TABLE 6

Long Term Stability of Terpenes Stored at Room Temperature (Flavor and Fragrance).
Night Cap 3 g Infused Flower/Pre-Roll (Sample ID = 221209R012)

| Analysis | Result (%) Jan. 18, 2022 | Result (%) - Dec. 9, 2022 | Terpene Type | Flavor | Fragrance |
|---|---|---|---|---|---|
| Total Terpenes | 2.59% | 2.42% | | | |
| Linalool | 0.851 | 0.846 | monoterpene alcohol | citrus-like flavor with spicy tropical accent | floral, spicy wood, like lavender |
| Limonene | 0.384 | 0.341 | monoterpene | citrus | citrus |
| Myrcene | 0.344 | 0.394 | monoterpene | earthy, grassy, mildly sweet | dank, spicy, earthy and musky |
| β-Caryophyllene | 0.321 | 0.264 | bicyclic sesquiterpene | earthy with hints of spice | earthy, bold, almost spicy, clove aroma |
| α-Bisabolol | 0.154 | 0.126 | monocyclic sesquiterpene alcohol | floral, peppery | sweet, floral |
| α-Humulene | 0.114 | 0.096 | sesquiterpene | spicy, herbaceous, or woody, like beer hops | earthy, woody, spicy |
| α-Pinene | 0.111 | 0.118 | bicyclic monoterpene | earthy, herbaceous, slightly bitter | pine woodsy |
| trans-β-Farnesene | 0.082 | 0.062 | sesquiterpene | Mild, sweet, and warm woody | fruity, green apple |
| β-Pinene | 0.053 | 0.052 | bicyclic monoterpene | woody, spicy aromatic, like dill, parsley, basil | pine woodsy |
| Caryophyllene Oxide | 0.033 | 0.025 | bicyclic sesquiterpene | spicy | spicy, woody, like cinnamon and cloves |
| Terpineol | 0.024 | 0.023 | monoterpene alcohol | mint | lilac odor, sweet like peach |
| Nerolidol | 0.023 | 0.018 | sesquiterpene alcohol | green, floral, woody, citrus and melon | woody and like fresh bark |
| Fenchol | 0.021 | 0.021 | monoterpene alcohol | lightly bitter, spicy, citrus and earthy | pine, sweet, herbal, earthy |
| Guaiol | 0.021 | 0.015 | sesquiterpene alcohol | fruity | earthy, pine |
| Terpinolene | 0.009 | 0.006 | monoterpene | mint | piney, floral, herbaceous, slightly citrusy |
| Borneol | 0.009 | 0.009 | monoterpene alcohol | camphor-like | pungent, mint, metallic, |
| Nerol | 0.003 | 0.002 | monoterpene alcohol | green, floral, woody, citrus and melon | mixed rose and citrus |
| Sabinene Hydrate | 0.003 | 0.002 | monoterpene | citrus, wood, mint | citrus and pine |

In some embodiments, a fragrant and flavorful *Cannabis* plant product is made by replacing the aroma from one or more *Cannabis* varieties with a more desirable odor, for example, the chemistry of the formulation may be effective to substitute the acrid aroma of Kush and Cookies varieties with a "skunk-like" odor with a pleasant incense, frankincense or haze aroma.

Example 4. Consumer Evaluation of Exemplary Plant Products

*Cannabis* cigarettes of the plant product prepared as described in Examples 1A and 1B were given by the inventor (in compliance with all current State and local *Cannabis* (marijuana) laws, regulations, ordinances, and other requirements or orders issued by State or local government regulating the distribution, or transportation of *Cannabis* products), to a select group of highly experienced professional *Cannabis* cultivators and extractors for purposes of evaluation. The methods and processes used in the production of the plant material were not disclosed. After consumption, the experts were asked to characterize the organoleptic experience of the product and its origin. None of the experts guessed that the product was processed. All of the experts stated that the product was the result of a new cure method that locked the organoleptics of fresh *Cannabis* at the moment that it reached peak cure during the drying process.

Example 5. Formulations with Defined Chemistry

A. Exemplary CBD-Dominant Formulation with Defined Chemistry.

In one exemplary formulation having defined chemistry, the components of the final formulation of the fragrant and flavorful *Cannabis* plant product were the following:

76.2% dried and chopped plant material n-Alkanes: n-heptacosane 0.50%, n-nonacosane 0.50%

Fragrant and flavorful compounds (monoterpenes, terpene alcohols, sesquiterpenes, esters ethers, thiols, and aldehydes)

Monoterpenes: Limonene 0.85%, Myrcene 0.507%, alpha-Pinene 0.295%, beta-Pinene 0.145%, Valencene 0.0361%, alpha-Thujene 0.0176%, Farnesene 0.0095%, Ocimene 0.0080%

Terpene alcohols: Linalool 0.315%, Bisabolol 0.0661%, Guaiol 0.0551%, Terpineol 0.0363%, Nerolidol 0.0204%, Fenchol 0.0192%, Nerol 0.0055%, Borneol 0.0054%

Sesquiterpenes: beta-Caryophyllene 0.8832%, Humulene 0.4201%, Caryophyllene oxide 0.0460%

Esters: Linalyl acetate 0.025%
Ethers: 1,8 Cineole—0.0251%
Thiols: 3-methyl-2-butane-1-thiol 0.0041%
Aldehydes: Neral 0.0023%
Acidic cannabinoids: CBD 16%, CBCA 0.22%, CBGA 0.15%, THCVA 0.14%, CBDA 0.043%

B. Exemplary THC-Dominant Formulation with Defined Chemistry.

In another exemplary formulation having defined chemistry, the final formulation is similar to that provided in Example 5A, with the exception that the amount of biomass is decreased below 76.2% and the acidic cannabinoids in the formulation are changed to the following.

Acidic cannabinoids: THCa 30%, CBCA 0.22%, CBGA 0.15%, THCVA 0.14%, CBDA 0.043%

Example 6. Method for Making a Fragrant and Flavorful THC-Dominant EOI Extract Freshly harvested *Cannabis* from the Purple Punch cultivar containing flowers and trichomes was analyzed for cannabinoid and terpene content, frozen and transported to a manufacturing site, where the frozen plant material was placed in a ultra-low temperature freezer at −90° F., then extracted at −120° F. with pressurized isobutane in a Bizzy-bee Bipod extractor monitored spectroscopically in real time. The live resin extracted from the plant material was collected and decanted into glass jars and allowed to rest to at 55° F. to encourage the gradual off-gassing of the isobutane. During this off-gassing process, a small crystal of THCA was introduced into the jar to encourage nucleation of THCA in the resin to precipitate as crystalline THCA. Once the material had reached an equilibrium, >50% of the THCA was removed through centrifugation and mechanical separation. The remaining resin is now termed HTE (high terpene extract). Steam distilled terpenoids from *Cannabis* were combined with HTE. Ethers and esters extracted from *Cannabis* were added. Alkanes were added. The mixture was homogenized. The resulting EOI was analytically tested for cannabinoid and terpenoid content. The EOI was measured and blended into the chopped dried plant biomass with a ribbon blender.

In order to meet the specifications of the CBD-dominant formulation described in Example 5A, the THCa-reduced EOI extract was supplemented such that the final formulation of the fragrant and flavorful *Cannabis* plant product will be the following:

n-Alkanes: n-heptacosane 0.50%, n-nonacosane 0.50%
Fragrant and flavorful compounds (monoterpenes, terpene alcohols, sesquiterpenes, esters ethers, thiols, and aldehydes)
    Monoterpenes: Limonene 0.85%, Myrcene 0.507%, alpha-Pinene 0.295%, beta-Pinene 0.145%, Valencene 0.0361%, alpha-Thujene 0.0176%, Farnesene 0.0095%, Ocimene 0.0080%
    Terpene alcohols: Linalool 0.315%, Bisabolol 0.0661%, Guaiol 0.0551%, Terpineol 0.0363%, Nerolidol 0.0204%, Fenchol 0.0192%, Nerol 0.0055%, Borneol 0.0054%
    Sesquiterpenes: beta-Caryophyllene 0.8832%, Humulene 0.4201%, Caryophyllene oxide 0.0460%
    Esters: Linalyl acetate 0.025%
    Ethers: 1,8 Cineole—0.0251%
    Thiols: 3-methyl-2-butane-1-thiol 0.0041%
    Aldehydes: Neral 0.0023%
Acidic cannabinoids: CBD 16%, CBCA 0.22%, CBGA 0.15%, THCVA 0.14%, CBDA 0.043%

Following confirmation of compliance with the specification of the formulation, the EOI extract is packaged and shipped across state lines in compliance with local, state, federal and international regulations.

What is claimed is:

1. A fragrant and flavorful *Cannabis* plant product with a formulation comprising a mixture of (a) dried and chopped plant material from one or more *Cannabis* plant types, and (b) an Entourage of Interest (EOI) extract from one or more *Cannabis* plant types comprising one or more lipids, and one or more fragrant and flavorful compounds, wherein the one or more fragrant and flavorful compounds include one or more terpenes, and wherein at least 50% of the one or more terpenes are stably maintained in the *Cannabis* plant product when the plant product is stored at room temperature for 30 days or longer.

2. The fragrant and flavorful cannabis plant product of claim 1, wherein the EOI extract includes THCa and the EOI extract that has been treated to reduce the amount of THCa resulting in a THCa-reduced EOI extract.

3. The fragrant and flavorful cannabis plant product of claim 1, wherein the EOI extract, the dried and chopped plant material substrate or the cannabis plant product is supplemented with THCa or THC.

4. The fragrant and flavorful cannabis plant product of claim 3, wherein the cannabis plant product is supplemented with crystalline THCa and/or a cannabinoid isolate or distillate.

5. The fragrant and flavorful cannabis plant product of claim 1, wherein the cannabis plant type is a marijuana cultivar selected from the group consisting of *Cannabis sativa* subsp. *sativa* var. *sativa*, *Cannabis sativa* subsp. *sativa* var. *spontanea*, *Cannabis sativa* subsp. *indica* var. *indica*, *Cannabis sativa* subsp. *indica* var. *afghanica*, *Cannabis sativa* subsp. *indica* var. *himalayensis*, and *Cannabis sativa* subsp. *indica* var. *asperrima*.

6. The fragrant and flavorful cannabis plant product of claim 1, wherein at least 70%, of the one or more terpenes in the cannabis plant product are stably maintained for at least 30 days when stored at room temperature.

7. The fragrant and flavorful cannabis plant product of claim 1, wherein the one or more terpenes comprise monoterpenes, diterpenes and/or sesquiterpenes.

8. The fragrant and flavorful cannabis plant product of claim 1, wherein the cannabis plant product is supplemented with fragrant and flavorful compounds.

9. The fragrant and flavorful cannabis plant product of claim 1, wherein the total cannabinoid content in the cannabis plant product is from about 0.1% to 45% cannabinoids.

10. The fragrant and flavorful cannabis plant product of claim 7, wherein the one or more terpenes in the cannabis plant product include one or more of β-caryophyllene, β-myrcene, limonene, linalool, α-humulene, β-pinene, α-pinene, α-bisabolol, α-terpinene, β-ocimene, camphene, caryophyllene oxide, cis-nerolidol, γ-3-carene, eucalyptol, γ-terpinene, geraniol, ocimene, (−)-guaiol, (−)-isopulegol, p-cymene, terpinolene, trans-nerolidol, gerol, geranyl acetate, α-terpineol, α-phellanderene, sabinene, thymol, cedrene, cedrol, fenchol, valencene, α-thujene, and cymene.

11. The fragrant and flavorful cannabis plant product of claim 10, wherein the total monoterpene content in the cannabis plant product is from 1% to 10%.

12. The fragrant and flavorful cannabis plant product of claim 7, wherein the total sesquiterpene content in the cannabis plant product is less than 2%.

13. The fragrant and flavorful cannabis plant product of claim 1, further comprising from about 0.2 to 4.0% micro pulverized cannabis leaf.

14. The fragrant and flavorful cannabis plant product of claim 1, wherein the dried and chopped plant material further comprises one or more of hops, basil, mimosa, passion flower, corn silk, rose petals, lotus leaf, licorice root, jasmine, ginseng, red clover flowers, bergamot, lemon, lime, sweet orange, tangerine, mandarin, cinnamon bark, citronella, lemongrass, petitgrain, palmarosa, patchouli leaves, geranium, lavender, rosemary, spike lavender, ginger, vetiver, jasmine, neroli (orange blossom), and ylang-ylang.

15. The fragrant and flavorful cannabis plant product of claim 1, packaged as a pre-roll or cigarette form.

16. The fragrant and flavorful cannabis plant product of claim 1, wherein the cannabis plant product is supplemented with one or more powdered or liquid cannabinoids.

17. The fragrant and flavorful cannabis plant product of claim 8, wherein the cannabis plant product is supplemented with one or more powdered or liquid cannabinoids.

18. A fragrant and flavorful *Cannabis* plant product with a formulation having defined chemistry comprising a mixture of (a) dried and chopped plant material from a marijuana cultivar, and (b) an Entourage of Interest (EOI) extract comprising fragrant and flavorful compounds, wherein the fragrant and flavorful compounds are stably maintained in the *Cannabis* plant product when the plant product is stored at room temperature for 30 days or longer, wherein the marijuana cultivar is *Cannabis sativa* subsp. *indica* var. *indica*, and wherein the fragrant and flavorful compounds include limonene and myrcene, wherein at least 50% of the limonene and myrcene in the cannabis plant product are stably maintained for at least 30 days when stored at room temperature.

19. The fragrant and flavorful cannabis plant product of claim 18, wherein the EOI extract includes THCa and the EOI extract that has been treated to reduce the amount of THCa resulting in a THCa-reduced EOI extract.

20. The fragrant and flavorful cannabis plant product of claim 18, wherein the EOI extract, the dried and chopped plant material substrate or the cannabis plant product is supplemented with THCa or THC.

21. The fragrant and flavorful cannabis plant product of claim 20, wherein the cannabis plant product is supplemented with crystalline THCa and/or a cannabinoid isolate or distillate.

22. The fragrant and flavorful cannabis plant product of claim 18, packaged as a pre-roll or cigarette form.

23. The fragrant and flavorful cannabis plant product of claim 1, wherein at least 90% of the one or more terpenes in the cannabis plant product are stably maintained for at least 30 days when stored at room temperature.

24. The fragrant and flavorful cannabis plant product of claim 18, wherein at least 70% of the limonene and myrcene in the cannabis plant product are stably maintained for at least 30 days when stored at room temperature.

25. The fragrant and flavorful cannabis plant product of claim 18, wherein at least 90% of the limonene and myrcene in the cannabis plant product are stably maintained for at least 30 days when stored at room temperature.

* * * * *